US005821336A

United States Patent [19]
Odink et al.

[11] Patent Number: 5,821,336
[45] Date of Patent: Oct. 13, 1998

[54] CYTOKINE WHICH MEDIATES INFLAMMATION

[75] Inventors: Karel Gerrit Odink, Rheinfelden, Switzerland; Lajos Tarcsay, Grenzach-Wyhlen, Germany; Josef Brüggen, Schützengasse, Switzerland; Walter Wiesendanger, Aesch, Switzerland; Nico Cerletti, Bottmingen, Switzerland; Clemens Sorg, Münster, Germany; Christiane DeWolf-Peeters, Bekkevoort; Jan Delabie, Zwingstraat, both of Belgium

[73] Assignee: Novartis Coporation, Summit, N.J.

[21] Appl. No.: 714,927

[22] Filed: Sep. 27, 1996

Related U.S. Application Data

[60] Continuation of Ser. No. 310,025, Sep. 21, 1994, abandoned, which is a division of Ser. No. 811,893, Dec. 20, 1991, Pat. No. 5,411,882, which is a continuation of Ser. No. 546,344, Jun. 29, 1990, abandoned.

[30] Foreign Application Priority Data

Jul. 5, 1989 [GB] United Kingdom .................... 8915414

[51] Int. Cl.$^6$ .............................. C07K 14/52; C12N 15/63
[52] U.S. Cl. .......................... 530/351; 530/412; 530/416; 530/417; 435/69.5; 435/70.1; 435/71.1; 435/71.2; 435/172.3; 435/325; 435/252.3; 435/252.31; 435/252.34; 435/253.4; 435/254.11; 435/255.1; 435/255.2; 435/366
[58] Field of Search ..................... 530/351, 412, 530/416, 417; 435/69.5, 70.1, 71.1, 71.2, 172.3, 325, 252.3, 252.31, 252.34, 253.4, 254.11, 255.1, 255.2, 366

[56] References Cited

FOREIGN PATENT DOCUMENTS 0237073  3/1987  European Pat. Off. .
0310136  10/1988  European Pat. Off. .

OTHER PUBLICATIONS

Bryant, J., et al., "Cloning and Expression of a Smooth Muscle Caldesmon", *J. Biol. Chem.*, 264(23):13873–13879 (1989).
Burmeister, G., et al., "Generation and Characterization of a Monoclonal Antibody (IC5) to Human Migration Inhibitory Factor (MIF)", *Immunobiol.*, 171:461–474 (1986).
Clemens, S., et al., Abstract Only, E.P. Appl. 162,812, "Lymphokine in the Pure State, Monoclonal Antibodies, Hybridoma Cell Lines, and Applications", *Chemical Abstract*, 104(25):223451q (1985).
Itakura, K., et al., "Synthesis and Use of Synthetic Oligonucleotides", *Ann. Rev. Biochem.*, 53:323–356 (1984).
Lemaire, C., et al., "Nucleotide Sequence of Chicken Dystrophin cDNA", *Nucleic Acids Research*, 16(24):11815–11816 (1988).
Maniatis, et al., *Molecular Cloning, A Laboratory Manual*, 2nd Ed., 1.74–1.91, 7.12–7.15, 8.3–8.26, 8.46–8.52, 9.4–9.15, 15.3–15.4, 15.14–15.19, 15.51–15.52, 16.3–16.8 16.30–16.31, 16.8–16.16 (1989).

McNally, E., et al., "Complete Nucleotide Sequence of Full Length cDNA for Rat α Cardiac Myosin Heavy Chain", *Nucleic Acids Research*, 17(18):7527–7528 (1989).
Mellon, P., et al., "Identification of DNA Sequences Required for Transcription of the Human α1–Globin Gene in a New SV40 Host–Vector System", *Cell*, 27:279–288 (1981).
Molina, M.I. et al., "The Sequences of an Embryonic Myosin Heavy Chain Gene and Isolation of Its Corresponding cDNA", *J. Biol. Chem.*, 262(14):6478–6488 (1987).
Odink, K., et al., "Two Calcium–binding Proteins in Infiltrate Macrophages of Reumatoid Arthritis", *Nature*, 330:80–82 (1987).
Odink, K.G., et al., Abstract Only, E.P. Appl. 263,072, "Cloning, Sequencing, and Expression of Macrophage Migration Inhibition Factor Genes, Preparation of Antibodies to the Proteins, and Use of the Antibodies for Diagnosis of Inflammatory Disorders and Cystic Fibrosis", *Chemical Abstract*, 109(17):1439662 (1988).
Roitt, I.M., et al., "Cellular Reactions in Delayed Hypersensitivity", *Immunology*, Gower Medical Publishing, London, 22.5–22.6 (1985).
Saez, L., et al., "Characterization of Diverse Forms of Myosin Heavy Chain Expressed in Adult Human Skeletal Muscle", *Nucleic Acids Research*, 14(7):2951–2969 (1986).
Shimokawa, Y., et al., Lymphocyte Chemotaxis in Inflammation: VII. Isolation and Purification of Chemotactic Factors for T Lymphocytes from PPD–Induced Delayed Hypersensitivity Skin Reaction Site in the Guinea–Pig, *Immunology*, 51(2):275–285 (1984).
Steinert, P.M., et al., "Molecular and Cellular Biology of Intermediate Filaments", *Ann. Rev. Biochem.*, 57:593–625 (1988).
Ueda, K., et al., "The Chemical Mediation of Delayed Hypersensitivity Skin Reactions: III. Purification and Characterization of a Precursor Protein for Macrophage–Chemotactic Factor in Normal Guinea Pig Plasma", *American Journal of Pathology*, 108(3):291–298 (1982).
Weiser, W.Y., et al., "Molecular Cloning of a cDNA Encoding a Human Macrophage Migration Inhibitory Factor", *PNAS*, 86:7522–7526 (1989).
Young, R.A, "Efficient isolation of Genes by Using Antibody Probes", *PNAS*, 80:1194–1198 (1983).
Cunningham et al. (1989) Science vol. 244, pp. 1081–1085.
George et al. (1988) Macromolecular Sequencing & Synthesis chapter 12, pp. 127–149, Alan R. Liss, Inc., New York.

*Primary Examiner*—John Ulm
*Assistant Examiner*—Prema Mertz
*Attorney, Agent, or Firm*—Gregory D. Ferraro

[57] ABSTRACT

The invention concerns polypeptides with an apparent molecular weight of around 160 kD which are mediators or precursors for mediators of inflammation, derivatives thereof such as mutants and fragments, processes for their preparation, DNAs and hybrid vectors coding for the polypeptides and derivatives and host cells transformed with such hybrid vectors, polyclonal and monoclonal antibodies specific for the polypeptides or their derivatives and antibody derivatives as well as diagnostic and therapeutic methods for inflammatory conditions and Hodgkin lymphomas.

11 Claims, 10 Drawing Sheets

```
GCGGCGCAGG CGGCGGCGTC CGAGGAGATT TAATCCAGAG ACTGACTTCA      50

CTATAGAACC CACAGTTGTA TCAATGGTTG GGGAAAGATA GTGGCAACAG     100

GCAAAGGAGA AACAGCTCTG ACATACAAAG AAA ATG AGT ATG CTA      145
                                     Met Ser Met Leu
                                      1
AAG CCA AGT GGG CTT AAG GCC CCC ACC AAG ATC CTG AAG CCT    187
Lys Pro Ser Gly Leu Lys Ala Pro Thr Lys Ile Leu Lys Pro
 5           10                  15

GGA AGC ACA GCS CTG AAG ACA CCT ACG GCT GTT GTA GCT CCA    229
Gly Ser Thr Ala Leu Lys Thr Pro Thr Ala Val Val Ala Pro
    20               25                  30

GTA GAA AAA ACC ATA TCC AGT GAA AAA GCA TCA AGC ACT CCA    271
Val Glu Lys Thr Ile Ser Ser Glu Lys Ala Ser Ser Thr Pro
        35                  40                  45

TCA TCT GAG ACT CAG GAG GAA TTT GTG GAT GAC TTT CGA GTT    313
Ser Ser Glu Thr Gln Glu Glu Phe Val Asp Asp Phe Arg Val
            50                  55                  60

GGG GAG CGA GTT TGG GTG AAT GGA AAT AAG CCT GGA TTT ATC    355
Gly Glu Arg Val Trp Val Asn Gly Asn Lys Pro Gly Phe Ile
                65                  70

CAG TTT CTT GGA GAA ACC CAG TTT GCA CCA GGC CAG TGG GCT    397
Gln Phe Leu Gly Glu Thr Gln Phe Ala Pro Gly Gln Trp Ala
 75                  80                  85

GGA ATT GTT TTA GAT GAA CCC ATA GGC AAG AAC GAT GGT TCG    439
Gly Ile Val Leu Asp Glu Pro Ile Gly Lys Asn Asp Gly Ser
     90                  95                  100
```

FIG.1A

```
GTG GCA GGA GTT CGG TAT TTC CAG TGT GAA CCT TTA AAG GGC    481
Val Ala Gly Val Arg Tyr Phe Gln Cys Glu Pro Leu Lys Gly
        105             110                 115

ATA TTT ACC CGA CCT TCA AAG TTA ACA AGG AAG GTG CAA GCA    523
Ile Phe Thr Arg Pro Ser Lys Leu Thr Arg Lys Val Gln Ala
        120             125                 130

GAA GAT GAA GCT AAT GGC CTG CAG ACA ACG CCC GCC TCC CGA    565
Glu Asp Glu Ala Asn Gly Leu Gln Thr Thr Pro Ala Ser Arg
            135                 140

GCT ACT TCA CCG CTG TGC ACT TCT ACG GCC AGC ATG GTG TCT    607
Ala Thr Ser Pro Leu Cys Thr Ser Thr Ala Ser Met Val Ser
145             150                 155

TCC TCC CCC TCC ACC CCT TCA AAC ATC CCT CAG AAA CCA TCA    649
Ser Ser Pro Ser Thr Pro Ser Asn Ile Pro Gln Lys Pro Ser
        160             165                 170

CAG CCA GCA GCA AAG GAA CCT TCA GCT ACG CCT CCG ATC AGC    691
Gln Pro Ala Ala Lys Glu Pro Ser Ala Thr Pro Pro Ile Ser
        175             180                 185

AAC CTT ACA AAA ACT GCC AGT GAA TCT ATC TCC AAC CTT TCA    733
Asn Leu Thr Lys Thr Ala Ser Glu Ser Ile Ser Asn Leu Ser
        190             195                 200

GAG GCT GGC TCA ATC AAG AAA GGA GAA AGA GAG CTC AAA ATC    775
Glu Ala Gly Ser Ile Lys Lys Gly Glu Arg Glu Leu Lys Ile
            205                 210

GGA GAC AGA GTA TTG GTT GGT GGC ACT AAG GCT GGT GTA GTC    817
Gly Asp Arg Val Leu Val Gly Gly Thr Lys Ala Gly Val Val
215             220                 225

CGG TTT CTT GGG GAG ACC GAC TTT GCC AAG GGG GAG TGG TGT    859
Arg Phe Leu Gly Glu Thr Asp Phe Ala Lys Gly Glu Trp Cys
        230             235                 240

GGC GTG GAG TTA GAT GAG CCA CTT GGG AAG AAT GAT GGC GCT    901
Gly Val Glu Leu Asp Glu Pro Leu Gly Lys Asn Asp Gly Ala
            245                 250                 255

GTT GCT GGA ACA AGG TAT TTT CAG TGT CAA CCC AAA TAT GGC    943
Val Ala Gly Thr Arg Tyr Phe Gln Cys Gln Pro Lys Tyr Gly
            260                 265                 270

TTG TTC GCT CCT GTC CAC AAA GTT ACC AAG ATT GGC TTC CCT    985
Leu Phe Ala Pro Val His Lys Val Thr Lys Ile Gly Phe Pro
                275                 280
```

FIG. 1B

```
TCC ACT ACA CCA GCC AAA GCC AAG GCC AAC GCA GTG AGG CGA   1027
Ser Thr Thr Pro Ala Lys Ala Lys Ala Asn Ala Val Arg Arg
285             290             295

GTG ATG GCG ACC ACG TCC GCC AGC CTG AAG CGC AGC CCT TCT   1069
Val Met Ala Thr Thr Ser Ala Ser Leu Lys Arg Ser Pro Ser
    300             305             310

GCC TCT TCC CTC AGC TCC ATG AGC TCA GTG GCC TCC TCT GTG   1111
Ala Ser Ser Leu Ser Ser Met Ser Ala Ser Ser Val Ser Ser
        315             320             325

AGC AGC AGG CCC AGT CGG ACA GGA CTA TTG ACT GAA ACC TCC   1153
Ser Val Arg Pro Ser Arg Thr Gly Leu Leu Thr Glu Thr Ser
            330             335             340

TCC CGT TAC GCC AGG AAG ATC TCC GGT ACC ACT GCC CTC CAG   1195
Ser Arg Tyr Ala Arg Lys Ile Ser Gly Thr Thr Ala Leu Gln
                345             350

GAG GCC CTG AAG GAG AAG CAG CAG CAC ATT GAG CAG CTG CTG   1237
Glu Ala Leu Lys Glu Lys Gln Gln His Ile Glu Gln Leu Leu
355             360             365

GCG GAA CGG GAT CTG GAG AGG GCG GAG GTG GCC AAG GCC ACG   1279
Ala Glu Arg Asp Leu Glu Arg Ala Glu Val Ala Lys Ala Thr
    370             375             380

AGC CAC GTG GGG GAG ATA GAG CAG GAG CTA GCT CTG GCC CGG   1321
Ser His Val Gly Glu Ile Glu Gln Glu Leu Ala Leu Ala Arg
        385             390             395

GAC GGA CAT GAC CAG CAT GTC CTG GAA TTG GAA GCC AAA ATG   1363
Asp Gly His Asp Gln His Val Leu Glu Leu Glu Ala Lys Met
            400             405             410

GAC CAG CTG CGA ACA ATG GTG GAA GCT GCT GAC AGG GAG AAG   1405
Asp Gln Leu Arg Thr Met Val Glu Ala Ala Asp Arg Glu Lys
                415             420

GTG GAG CTT CTC AAC CAG CTT GAA GAG GAG AAA AGG AAG GTT   1447
Val Glu Leu Leu Asn Gln Leu Glu Glu Glu Lys Arg Lys Val
425             430             435

GAG GAC CTT CAG TTC CGG GTT GAA GAA GAA TCA ATT ACC AAA   1489
Glu Asp Leu Gln Phe Arg Val Glu Glu Glu Ser Ile Thr Lys
    440             445             450

GGT GAT CTT GAG ACG CAG ACC AAA CTG GAG CAT GCC CGC ATT   1531
Gly Asp Leu Glu Thr Gln Thr Lys Leu Glu His Ala Arg Ile
        455             460             465
```

FIG.1C

```
AAG GAG CTT GAA CAG AGC CTG CTC STT GAA AAG ACC AAA GCT    1573
Lys Glu Leu Glu Gln Ser Leu Leu Phe Glu Lys Thr Lys Ala
            470                 475                 480

GAC AAA CTC CAG AGG GAG TTA GAA GAC ACT AGG GTG GCT ACA    1615
Asp Lys Leu Gln Arg Glu Leu Glu Asp Thr Arg Val Ala Thr
            485                 490

GTT TCA GAA AAG TCA CGT ATA ATG GAA CTG GAG AAA GAC CTA    1657
Val Ser Glu Lys Ser Arg Ile Met Glu Leu Glu Lys Asp Leu
495                 500                 505

GCA TTG AGA GTA CAG GAA GTA GCT GAG CTC CGA AGA AGG CTA    1699
Ala Leu Arg Val Gln Glu Val Ala Glu Leu Arg Arg Arg Leu
            510                 515                 520

GAG TCC AAT AAG CCT GCT GGG GAT GTG GAC ATG TCA CTT TCC    1741
Glu Ser Asn Lys Pro Ala Gly Asp Val Asp Met Ser Leu Ser
            525                 530                 535

CTT TTG CAA GAG ATA AGC TCT TTG CAA GAA AAG TTA GAA GTC    1783
Leu Leu Gln Glu Ile Ser Ser Leu Gln Glu Lys Leu Glu Val
            540                 545                 550

ACC CGT ACT GAC CAC CAG AGA GAA ATA ACT TCT CTG AAG GAG    1825
Thr Arg Thr Asp His Gln Arg Glu Ile Thr Ser Leu Lys Glu
                555                 560

CAT TTT GGA GCC CGG GAA GAA ACT CAT CAG AAG GAG ATA AAG    1867
His Phe Gly Ala Arg Glu Glu Thr His Gln Lys Glu Ile Lys
565                 570                 575

GCT CTG TAT ACC GCC ACG GAA AAG CTT TCC AAA GAG AAC GAG    1909
Ala Leu Tyr Thr Ala Thr Glu Lys Leu Ser Lys Glu Asn Glu
            580                 585                 590

TCA TTG AAA AGC AAG CTG GAG CAT GCC AAC AAA GAG AAC TCA    1951
Ser Leu Lys Ser Lys Leu Glu His Ala Asn Lys Glu Asn Ser
            595                 600                 605

GAT GTG ATA GCT CTA TGG AAG TCC AAA CTG GAG ACT GCC ATC    1993
Asp Val Ile Ala Leu Trp Lys Ser Lys Leu Glu Thr Ala Ile
            610                 615                 620

GCA TCC CAC CAG CAG GCG ATG GAA GAA CTG AAG GTA TCT TTC    2035
Ala Ser His Gln Gln Ala Met Glu Glu Leu Lys Val Ser Phe
                625                 630

AGC AAA GGG CTT GGA ACA GAG ACG GCA GAA TTT GCT GAA CTA    2077
Ser Lys Gly Leu Gly Thr Glu Thr Ala Glu Phe Ala Glu Leu
635                 640                 645
```

FIG.1D

```
AAA ACA CAA ATA GAG AAA ATG AGA CTA GAT TAC CAA CAC GAA    2119
Lys Thr Gln Ile Glu Lys Met Arg Leu Asp Tyr Gln His Glu
        650             655             660

ATA GAA AAT TTG CAG AAT CAA CAA GAC TCT GAA CGG GCT GCC    2161
Ile Glu Asn Leu Gln Asn Gln Gln Asp Ser Glu Arg Ala Ala
            665             670             675

CAT GCT AAA GAG ATG GAA GCC TTG AGG GCT AAA CTG ATG AAA    2203
His Ala Lys Glu Met Glu Ala Leu Arg Ala Lys Leu Met Lys
                680             685             690

GTT ATT AAA GAA AAG GAA AAC AGT CTG GAA GCC ATC AGG TCG    2245
Val Ile Lys Glu Lys Glu Asn Ser Leu Glu Ala Ile Arg Ser Lys Leu
                    695             700

AAA CTG GAC AAA GCA GAA GAC CAG CAT CTC GTA GAA ATG GAA    2287
Ala Ile Asp Lys Ala Glu Asp Gln H4s Leu Val Glu Met Glu
705             710             715

GAC ACG TTA AAC AAA TTA CAG GAA GCT GAA ATA AAG GTA AAG    2329
Asp Thr Leu Asn Lys Leu Gln Glu Ala Glu Ile Lys Val Lys
        720             725             730

GAG CTA GAG GTA CTG CAA GCC AAA TGC AAT GAA CAA ACC AAG    2371
Glu Leu Glu Val Leu Gln Ala Lys Cys Asn Glu Gln Thr Lys
            735             740             745

GTT ATT GAT AAT TTT ACA TCA CAG CTC AAG GCT ACT GAA GAA    2413
Val Ile Asp Asn Phe Thr Ser Gln Leu Lys Ala Thr Glu Glu
                750             755             760

AAG CTC TTG GAT CTT GAT GCA CTT CGG AAA GCC AGT TCC GAA    2455
Lys Leu Leu Asp Leu Asp Ala Leu Arg Lys Ala Ser Ser Glu
                    765             770

GGT AAA TCG GAA ATG AAG AAA CTT AGA CAG CAG CTT GAG GCA    2497
Gly Lys Ser Glu Met Lys Lys Leu Arg Gln Gln Leu Glu Ala
775             780             785

GCT GAG AAA CAG ATT AAA CAT TTA GAG ATT GAA AAG AAT GCT    2539
Ala Glu Lys Gln Ile Lys His Leu Glu Ile Glu Lys Asn Ala
        790             795             800

GAA AGT AGC AAG GCT AGT AGC ATT ACC AGA GAG CTC CAG GGG    2581
Glu Ser Ser Lys Ala Ser Ser Ile Thr Arg Glu Leu Gln Gly
            805             810             815

AGA GAG CTA AAG CTT ACT AAC CTT CAG GAA AAT TTG AGT GAA    2623
Arg Glu Leu Lys Leu Thr Asn Leu Gln Glu Asn Leu Ser Glu
                820             825             830
```

FIG.1E

```
GTC AGT CAA GTG AAA GAG ACT TTG GAA AAA GAA CTT CAG ATT   2665
Val Ser Gln Val Lys Glu Thr Leu Glu Lys Glu Leu Gln Ile
            835                     840

TTG AAA GAA AAG TTT GCT GAA GCT TCA GAG GAG GCA GTC TCT   2707
Leu Lys Glu Lys Phe Ala Glu Ala Ser Glu Glu Ala Val Ser
845                 850                 855

GTT CAG AGA AGT ATG CAA GAA ACT GTA AAT AAG TTA CAC CAA   2749
Val Gln Arg Ser Met Gln Glu Thr Val Asn Lys Leu Hia Gln
        860                 865                 870

AAG GAG GAA CAG TTT AAC ATG CTG TCT TCT GAC TTG GAG AAG   2791
Lys Glu Glu Gln Phe Asn Met Leu Ser Ser Asp Leu Glu Lys
                875                 880                 885

CTG AGA GAA AAC TTA GCA GAT ATG GAG GCA AAA TTT AGA GAG   2833
Leu Arg Glu Asn Leu Ala Asp Met Glu Ala Lys Phe Arg Glu
                890                 895                 900

AAA GAT GAG AGA GAA GAG CAG CTG ATA AAG GCA AAG GAA AAA   2875
Lys Asp Glu Arg Glu Glu Gln Leu Ile Lys Ala Lys Glu Lys
                    905                 910

CTG GAA AAT GAC ATT GCA GAA ATA ATG AAG ATG TCA GGA GAT   2917
Leu Glu Asn Asp Ile Ala Glu Ile Met Lya Met Ser Gly Asp
915                 920                 925

AAC TCT TCT CAG CTG ACA AAA ATG AAC GAT GAA TTA CGT CTG   2959
Asn Ser Ser Gln Leu Thr Lys Met Asn Asp Glu Leu Arg Leu
        930                 935                 940

AAA GAA AGA GAT GTA GAA GAA TTA CAG CTA AAA CTT ACA AAG   3001
Lys Glu Arg Asp Val Glu Glu Leu Gln Leu Lys Leu Thr Lys
            945                 950                 955

GCT AAT GAA AAT GCA AGT TTT CTG CAA AAA AGT ATT GAG GAC   3043
Ala Asn Glu Asn Ala Ser Phe Leu Gln Lys Ser Ile Glu Asp
                960                 965                 970

ATG ACT GTC AAA GCT GAA CAG AGC CAG CAA GAA GCA GCT AAA   3085
Met Thr Val Lys Ala Glu Gln Ser Gln Gln Glu Ala Ala Lya
                    975                 980

AAG CAT GAG GAA GAA AAG AAA GAA TTG GAG AGG AAA TTG TCG   3127
Lys His Glu Glu Glu Lys Lys Glu Leu Glu Arg Lys Leu Ser
985                 990                 995

GAC CTG GAA AAG AAA ATG GAA ACA AGC CAC AAC CAG TGT CAG   3169
Asp Leu Glu Lys Lys Met Glu Thr Ser Hia Asn Gln Cys Gln
    1000                1005                1010
```

FIG. 1F

```
GAG CTG AAA GCC AGG TAT GAG AGA GCC ACT TCT GAG ACA AAA      3211
Glu Leu Lys Ala Arg Tyr Glu Arg Ala Thr Ser Glu Thr Lys
        1015                1020                1025

ACC AAG CAT GAA GAA ATC CTA CAG AAC CTC CAG AAG ACG CTG      3253
Thr Lys His Glu Glu Ile Leu Gln Asn Leu Gln Lys Thr Leu
        1030                1035                1040

CTG GAC ACA GAG GAC AAG CTG AAG GGC GCA CGG GAG GAG AAC      3295
Leu Asp Thr Glu Asp Lys Leu Lys Gly Ala Arg Glu Glu Asn
        1045                1050

AGT GGC TTG CTG CAG GAG CTG GAG GAG CTO AGA AAG CAA GCC      3337
Ser Gly Leu Leu Gln Glu Leu Glu Glu Leu Arg Lys Gln Ala
1055            1060                1065

GAC AAA GCC AAA GCT GCT CAA ACA GCG GAA GAT GCC ATG CAG      3379
Asp Lys Ala Lys Ala Ala Gln Thr Ala Glu Asp Ala Met Gln
        1070                1075                1080

ATA ATG GAA CAG ATG ACC AAA GAG AAG ACT GAG ACT CTG GCC      3421
Ile Met Glu Gln Met Thr Lys Glu Lys Thr Glu Thr Leu Ala
        1085                1090                1095

TCC TTG GAG GAC ACC AAG CAA ACA AAT GCA AAA CTA CAG AAT      3463
Ser Leu Glu Asp Thr Lys Gln Thr Asn Ala Lys Leu Gln Asn
        1100                1105                1110

GAA TTG GAC ACA CTT AAA GAA AAC AAC TTG AAA AAT GTG GAA      3505
Glu Leu Asp Thr Leu Lys Glu Asn Asn Leu Lys Asn Val Glu
            1115                1120

GAG CTG AAC AAA TCA AAA GAA CTC CTG ACT GTA GAG AAT CAA      3547
Glu Leu Asn Lys Ser Lys Glu Leu Leu Thr Val Glu Asn Gln
1125            1130                1135

AAA ATG GAA GAA TTT AGG AAA GAA ATA GAA ACC CTA AAG CAG      3589
Lys Met Glu Glu Phe Arg Lys Glu Ile Glu Thr Leu Lys Gln
        1140                1145                1150

GCA GCA GCT CAG AAG TCC CAG CAG CTT TCA GCG TTG CAA GAA      3631
Ala Ala Ala Gln Lys Ser Gln Gln Leu Ser Ala Leu Gln Glu
        1155                1160                1165

GAG AAC GTT AAA CTT GCT GAG GAG CTG GGG AGA AGC AGG GAC      3673
Glu Asn Val Lys Leu Ala Glu Glu Leu Gly Arg Ser Arg Asp
        1170                1175                1180

GAA GTC ACA AGT CAT CAA AAG CTG GAA GAA GAA AGA TCT GTG      3715
Glu Val Thr Ser His Gln Lys Leu Glu Glu Glu Arg Ser Val
            1185                1190
```

FIG.1G

```
CTC AAT AAT CAG TTG TTA GAA ATG AAA AAA AGA GAA TCC AAG    3757
Leu Asn Asn Gln Leu Leu Glu Met Lys Lys Arg Glu Ser Lys
1195                1200                1205

TTC ATA AAA GAC GCA GAT GAA GAG AAA GCT TCC TTG CAG AAA    3799
Phe Ile Lys Asp Ala Asp Glu Glu Lys Ala Ser Leu Gln Lys
    1210                1215                1220

TCC ATC AGT ATA ACT AGT GCC TTA CTC ACA GAA AAG GAT GCC    3841
Ser Ile Ser Ile Thr Ser Ala Leu Leu Thr Glu Lys Asp Ala
        1225                1230                1235

GAG CTG GAG AAA CTG AGA AAT GAG GTC ACA GTG CTC AGG GGA    3883
Glu Leu Glu Lys Leu Arg Asn Glu Val Thr Val Leu Arg Gly
            1240                1245                1250

GAA AAC GCC TCT GCC AAG TCC TTG CAT TCA GTT GTT CAG ACT    3925
Glu Asn Ala Ser Ala Lys Ser Leu His Ser Val Val Gln Thr
                1255                1260

CTA GAG TCT GAT AAG GTG AAG CTC GAG CTC AAG GTA AAG AAC    3967
Leu Glu Ser Asp Lys Val Lys Leu Glu Leu Lys Val Lys Asn
1265                1270                1275

TTG GAG CTT CAA CTC AAA GAA AAC AAG AGG CAG CTC AGC AGC    4009
Leu Glu Leu Gln Leu Lys Glu Asn Lys Arg Gln Leu Ser Ser
    1280                1285                1290

TCC TCA GGT AAT ACA GAC ACT CAG GCA GAC GAG GAT GAA AGA    4051
Ser Ser Gly Asn Thr Asp Thr Gln Ala Asp Glu Asp Glu Arg
        1295                1300                1305

GCC CAG GAG AGT CAG ATT GAT TTC CTA AAT TCA GTA ATA GTG   4093
 Ala Gln Glu Ser Gln Ile Asp Phe Leu Asn Ser Val Ile Val
             1310                1315                1320

GAC CTT CAA AGG AAG AAT CAA GAC CTC AAG ATG AAG GTG GAG   4135
 Asp Leu Gln Arg Lys Asn Gln Asp Leu Lys Met Lys Val Glu
                 1325                1330

ATG ATG TCA GAA GCA GCC CTG AAT GGG AAC GGG GAT GAC CTA   4177
 Met Met Ser Glu Ala Ala Leu Asn Gly Asn Gly Asp Asp Leu
 1335                1340                1345

AAC AAT TAT GAC AGT GAT GAT CAG GAG AAA CAG TCC AAG AAG   4219
 Asn Asn Tyr Asp Ser Asp Asp Gln Glu Lys Gln Ser Lys Lys
     1350                1355                1360

AAA CCT CGC CTC TTC TGT GAC A$T TGT GAC TGC TTT GAT CTC   4261
 Lys Pro Arg Leu Phe Cys Asp Ile Cya Asp Cys Phe Asp Leu
         1365                1370                1375
```

FIG.1H

```
CAC GAC ACA GAG GAT TGT CCT ACC CAG GCA CAG ATG TCA GAG    4303
His Asp Thr Glu Asp Cys Pro Thr Gln Ala Gln Met Ser Glu
         1380              1385              1390

GAC CCT CCC CAT TCC ACA CAC CAT GGC AGT CGG GGT GAG GAA    4345
Asp Pro Pro His Ser Thr His His Gly Ser Arg Gly Glu Glu
             1395              1400

CGC CCA TAC TGT GAA ATC TGT GAG ATG TTT GGA CAC TGG GCC    4387
Arg Pro Tyr Cys Glu Ile Cys Glu Met Phe Gly His Trp Ala
1405             1410              1415

ACC AAC TGC AAT GAC GAC GAA ACC TTC TGATGAAGCC             4424
Thr Asn Cys Asn Asp Asp Glu Thr Phe
    1420              1425
```

```
TCCAGTGGAG AACTGGGCTT GCTCAGACGC ACTCGCATTG ACACAACGTA    4474
ACACCAGCAT TGTGTGTGCA GACTTCAGGA GAACTCATGT TATTTTTTAA    4524
CCCCGTCAAC AAATCTAGGA AAATATTTTG.ATCTTCAACA AATTGCCCTT    4574
TAGTCTCCCC GTATGAGTTA GAATAATAAA TATTTAGTAG GTGAGTTTTC    4624
ACCTCGAATT TTGTTTTCTT GATTTTTACG TTTGAAGACA TTGCACCAGA    4674
TGCCATTACA TTTATTGGCC CCCCGACCTT GTAGAAAAAC CCCTACCCTC    4724
ACAATACCTT ATTTAAGTAA CTTTAAATTA TGCCGTTACT TTTCATATTT    4774
GCACCTAAGA TATTTCCAGG CTGCATTTGT ATATTTAGAT TTTTTGGTTA    4824
AGCTTTGACA CTGGAATGAG TTGAAAAAAT GTGCCATTTT GCATTTTCAT    4874
CTACTCATTT AAAGTATTTT ATTCTTATTC AAAGAAATAT CTGAGCTCTT    4924
TGCACTACCT GTTATCAGTA GTGCCTTTAC TTCAGGCTTG ATAATACTTA    4974
GGTGTGATTA TAAAATCATG AAGCAGGTAA AGGGAGGGGC AAGCCCCAAA    5024
CTGCTGTGGG GACATTTTAT AATCTATATG CTGCACCCAC TTAATCTACT    5074
GTGGTGTTTT GTTTATTAGT TTTGCATAAT TCAGCTTCT ATATATTGTA     5124
TGTATATATT TTTTAAAAAT CTATATTTTG GGAAAAAAAC ATACACAATG    5174
TGTCTTTCTT TTTGGACATT TACCTTTTTG AAAAAGAkAA CACTTAAAAT    5224
GATCATTAGG ACATAACAGA CTAGGCCAGA CATAGCATCT TGTGGCTTTG    5274
```

FIG.1I

```
CAACCATTTT CATTTGTTTG TTTTCCTTTT ATTTCTTCAC CAGATTTAAA    5324
TAAAAGGAGG AATTTTCTCC AATTTTTTTT TCCTTCTCTG GCAGGTATCC    5374
CCAGCAGTCA ATTAACAATA AGCCAGTATA AAACACCTAA ATAACCAATC    5424
TACAATCTCC CTTCACAAGT TTTTTTACTG TTTTTAGATG AATGTACGAT    5474
CAGAAATTCA ACGTTAATAA TTCTGGATTT TCTTATCACA AAAAAGAAAA    5524
TGAAGGACCT CAAAGCACCT GAACAGTTTA TCGACCAGTT TGAATCTATT    5574
TATCTTCATT TGAATGTCTT CTAGATATGT AAAAAGTCAT AAAATGTATC    5624
TTCCATGCTA CATGTACAAT AAGAACTTCT ATAATTGTAT-ATATGCCTTT    5674
GATGTATTTT CCCCTCAAGA TTATCAACTG TGTGTTCGAC AGTGAATATT    5724
CAATCTGGTA CCAGTTGAAA TTTTTGGTTA TAAATGTAAT ACGAATTGTT    5774
TCACAAACAG AAAACATGTA AAGCAGTATT AAAATTTGGC CAAACAAGTG    5824
TTCTGTATCT ACTTTTAATA AATGGTTATT CTTT                    5858
```

FIG. 1J

CYTOKINE WHICH MEDIATES INFLAMMATION

This is a Continuation of Ser. No. 08/310,025, filed Sep. 21, 1994, now abandoned, which is a Divisional of Ser. No. 07/811,893, filed Dec. 20, 1991, now U.S. Pat. No. 5,411,882, which is a Continuation of Ser. No. 07/546,344, filed Jun. 29, 1990.

The invention concerns polypeptides with an apparent molecular weight of around 160 kD which are mediators or precursors for mediators of inflammation, derivatives thereof such as mutants and fragments, processes for their preparation, DNAs and hybrid vectors coding for said polypeptides and derivatives and host cells transformed with such hybrid vectors, polyclonal and monoclonal antibodies specific for said polypeptides or their derivatives and antibody derivatives as well as diagnostic and therapeutic methods for inflammatory conditions and Hodgkin lymphomas.

BACKGROUND OF THE INVENTION

Cytokines are biologically active, soluble polypeptide mediators which control the differentiation, activation and proliferation of various cell types of the immune system, for example the induction or modulation of macrophage functions. Examples of cytokines are the well characterized interferons, interleukins and colony stimulating factor, as well as macrophage migration inhibition factor (MIF) and macrophage activation factor (MAF) that display macrophage inhibition or activation properties, respectively.

Numerous activities have been attributed to cytokines although few of these can be ascribed to single molecules. For example, human MIF, which is thought to consist of a group of polypeptides, is defined in vitro in an assay which measures the inhibition of random migration of macrophages. In vivo, human MIF plays an important role in the early events of cellular immune reactions ("delayed type hypersensitivity") by its mediation of macrophage functions. Generally, the first exposure of a patient to an antigen produces no noticeable change, but the immune status of the recipient is clearly altered. Upon second contact with the antigen, the delayed hypersensitivity reaction is manifested by the infiltration of cells, beginning with a perivascular accumulation of lymphocytes and monocytes at the site where the antigen is located. Some of these cells are specifically sensitized as a result of the first contact with the antigen. These cells react with the antigen, which causes release of lymphokines and the attraction and retention of large numbers of unsensitized cells. In particular, it is assumed that the production of MIF results in the attraction of monocytes which pass through the endothelium of the blood vessel wall and enter the surrounding tissue. Concomittantly with this infiltration, the monocytes differentiate into tissue macrophages. The macroscopic phenomena seen in delayed type hypersensitivity are swelling at the site of contact with the antigen caused by cellular infiltration and reddening caused by dilatation of the underlying blood vessels. Under normal conditions, the inflammatory reaction will cease after about two to three days when possible tissue damage has been repaired. However, for unknown reasons, inflammations can become chronic, causing extensive tissue damage, e.g. rheumatoid arthritis. A possible explanation for the generation of chronic inflammation could be that, at the onset, the differentiation of the infiltrate macrophages has been deregulated.

OBJECT OF THE INVENTION

It is an object of the present invention to provide polypeptides, in particular human polypeptides, which are mediators or precursors for mediators of inflammation and derivatives thereof in high purity and sufficient quantity, and processes for their preparation. The problem of industrial polypeptide synthesis can be solved by the methods of recombinant DNA technology. It is therefore a further object of the invention to provide DNAs and hybrid vectors coding for the desired polypeptides and derivatives, and hosts transformed with such vectors. Other objects are methods of production of said DNAs, vectors and transformed host cells.

The polypeptides of the invention are useful for gaining a better understanding of the role of the mononuclear phagocyte system in clinically important areas such as resistance to infection, control of metastases, inflammatory processes and tissue repair. Furthermore, they are useful for the treatment of chronic inflammatory conditions. Accordingly, another object of the invention are pharmaceutical compositions comprising the polypeptides or derivatives thereof, and methods of their preparation. In addition, the polypeptides and derivatives according to the invention are useful for the study, identification and production of antagonists which can be used as anti-inflammatory drugs.

Another object of the invention is to provide antibodies specific for the polypeptides or the derivatives of the invention. Such antibodies can be used for the diagnosis of inflammatory conditions and to monitor the treatment of such conditions. Further these antibodies are useful for the diagnosis and treatment of Hodgkin lymphomas.

DESCRIPTION OF THE FIGURES

FIGS. 1(A–J): FIG. 1 provides amino acid and DNA sequence information for a mediator or a precursor for a mediator of inflammation.

DESCRIPTION OF THE INVENTION

The invention concerns polypeptides, in particular human polypeptides, with an apparent molecular weight of around 160 kD which are mediators or precursors for mediators of inflammation, and derivatives thereof.

Mediators of inflammation are chemical signal molecules which induce inflammatory reactions.

Precursors of polypeptide mediators are pre-stages of mediators, i.e. polypeptides which after their production are processed or trimmed, e.g. by cutting certain terminal amino acid sequences and/or by glycosylation, and are thereby converted into the active mediators, or retain their mediator activity if the precursor itself is an active mediator.

The polypeptides and derivatives of the invention play an important role in the immunological processes involved in inflammatory conditions. The inflammation mediator activity of the claimed polypeptides can for example be shown by their ability to induce localized inflammation when administered subcutaneously, for example in a normal guinea pig.

In general, the apparent molecular weight of a polypeptide of unknown structure can be determined according to conventional methods, e.g. by sedimentation analyses and determination of the diffusion coefficient or gel electrophoretic methods, in particular polyacrylamide gel electrophoresis in the presence of sodium dodecyl sulfate (SDS-PAGE).

In particular, the invention concerns a polypeptide which is a mediator or precursor for a mediator of inflammation designated MRP-160 of the amino acid sequence given in FIGS. 1(A–J), or derivatives thereof.

The calculated molecular weight of MRP-160 is 160,989.

Derivatives of the invention are mutants of the polypeptides according to the invention, in particular mutants of the polypeptides of the amino acid sequence given in FIGS. 1(A–J), wherein one or more single amino acids, in particular not more than 10% of the amino acids, are deleted or replaced by different amino acids, or additional amino acids are inserted.

Furthermore, derivatives of the invention are fragments of a polypeptide of the invention or of a mutant thereof, in particular fragments of a polypeptide of the amino acid sequence given in FIGS. 1(A–J) or of a mutant thereof, comprising at least 15 consecutive amino acids.

Preferred is a fragment which comprises amino acids 878 to 1427 of the amino acid sequence given in FIGS. 1(A–J) wherein the N-terminus is hydrogen, acyl, the amino acid sequence Asp-Gly-Ile-Asp-Lys-leu-Asp-Ile-Glu-Phe-Gly or the amino acid sequence Met-Asp-Gly-Ile-Asp-Lys-Leu-Asp-Ile-Glu-Phe-Gly. The fragment comprising the N-terminal amino acid sequence Met-Asp-Gly-Ile-Asp-Lys-Leu-Asp-Ile-Glu-Phe-Gly is designated rMRP-70.

The predicted molecular weight of the fragment designated rMRP-70 is 64,714 but on sodium dodecyl sulfate polyacrylamide gel electrophoresis (SDS-PAGE), this peptide migrates as a peptide of apparent molecular weight 70 kD when compared with standard marker proteins.

In addition, derivatives of the invention are compounds derived from a polypeptide, mutant or fragment according to the invention, in particular from MRP-160, a mutant or a fragment thereof, wherein functional groups, e.g. amino, hydroxy, mercapto or carboxy groups, are derivatized, e.g. glycosylated, acylated, amidated or esterified. In glycosylated derivatives a carbohydrate residue or an oligosaccharide is linked to asparagine, serine and/or threonine. Acylated derivatives are substituted by the acyl group of a naturally occurring organic or inorganic acid, e.g. formic acid, acetic acid, phosphoric acid or sulfuric acid, at amino groups, especially the N-terminal amino group, or at hydroxy groups, especially of tyrosine or serine. Esters are those of naturally occurring alcohols, e.g. of methanol or ethanol. Preferred are derivatives of the invention which are glycosylated.

Further derivatives of the invention are salts, especially pharmaceutically acceptable salts, for example metal salts, such as alkali metal and alkaline earth metal salts, e.g. sodium, potassium, magnesium, calcium or zinc salts, or ammonium salts formed with ammonia or a suitable organic amine, such as a lower alkylamine, e.g. triethylamine, hydroxy-lower alkylamine, e.g. 2-hydroxyethylamine, and the like.

Preferred are derivatives of polypeptides of the invention with an apparent molecular weight of 190 kD or with an apparent molecular weight of 140 kD which are produced by transfected cells or natural cells like endothelial cells. They can be observed by standard techniques such as Western blots.

The invention also concerns processes for the preparation of polypeptides which are mediators or precursors for mediators of inflammation, i.e. natural, recombinant or synthetic polypeptides, and derivatives according to the invention.

In one embodiment of the invention, such compounds are prepared by a process wherein a solution containing the polypeptides or derivatives according to the invention, for example an optionally pre-purified cell extract, cell supernatant or culture filtrate of stimulated normal human leukocytes or of genetically engineered microorganisms or continuous mammalian cell lines, is purified by chromatographic methods and, when required, the compounds are isolated and converted into derivatives thereof.

Cell extracts, cell supernatants and culture filtrates of stimulated normal human leukocytes containing natural polypeptides of the invention are prepared as for example described for MIF in the European Patent Application 0 162 812. In particular, normal human mononuclear cells are stimulated to produce lymphokines by suitable adjuncts, for example concanavalin A or phytohaemagglutinin, and are cultured according to customary methods. Optionally, cell extracts, cell supernatants or culture filtrates are then pre-purified by immunoaffinity chromatography.

Chromatographic methods contemplated for the preparation of the desired compounds are ion exchange chromatography, reversed phase high performance liquid chromatography, gel filtration, size exclusion chromatography, (immuno)affinity chromatography, chromatography on hydroxylapatite, hydrophobic interaction chromatography, and the like.

A suitable carrier material for ion exchange chromatography may be of organic or inorganic origin, e.g. cross-linked agarose, dextran, polyacrylamide, styrene/divinylbenzene copolymer, cellulose, or the like. This carrier material bears basic functional groups, e.g. tertiary amino functions, quarternary ammonium groups or acid functional groups, e.g. carboxylic or sulfonic acid residues. Examples for preferred ion exchangers are those bearing diethylaminoethyl (DEAE) or diethyl-2-hydroxypropylammonioethyl functional groups and those bearing sulfopropyl (SP) or carboxymethyl (CM) functional groups, either attached to carriers suitable for normal liquid chromatography, fast protein liquid chromatography (FPLC) or high performance liquid chromatography (HPLC). The separations and purifications with ion exchange chromatography are performed following established procedures, e.g. in aqueous buffer solutions of pH 5 to pH 9 containing increasing amounts of salt, for example sodium chloride.

Carrier material suitable for gel filtration or size exclusion chromatography includes cross-linked dextran, agarose, suitably modified polyacrylamide or silica, and the like. Optionally these carriers are modified with substituents bearing hydroxy functions, e.g. with 1-hydroxy- or 1,2-dihydroxy-lower alkyl groups. Such gel filtration or size exclusion chromatography may be performed on a column suitable for normal liquid chromatography, FPLC or HPLC as above using aqueous buffer solutions at a pH around neutrality containing variable amounts of salts, e.g. sodium chloride.

Reversed phase chromatography is performed on silica-based carrier material bearing hydrophobic groups, e.g. alkyl groups of 1 to 20 carbon atoms, preferably 4, 8, 12 or 18 carbon atoms or mixtures of alkyl groups of 1 and 8 or 12 and 18 carbon atoms, respectively, or phenyl groups. Related to this method is the hydrophobic interaction chromatography, wherein agarose or a related material coated with alkyl groups of up to 12 carbon atoms and/or phenyl groups is used. These chromatographic techniques are applied using FPLC or HPLC. Solvents for processing of the polypeptides of the invention on silica-based reversed phase material are aqueous acids, e.g. aqueous trifluoroacetic acid, containing increasing amounts of a polar, water-miscible organic solvent, e.g. acetonitrile, lower alcohols, e.g. methanol, ethanol or propanol, tetrahydrofuran, and the like, preferably acetonitrile.

Affinity chromatography is also contemplated for the purification of the polypeptides of the invention, using a suitable carrier material, e.g. cross-linked agarose, dextran or polyacrylamide bearing molecules with high affinity for a polypeptide or a derivative of the invention, mutants, fragments or derivatives thereof, for example bearing antibodies, in particular polyclonal and monoclonal antibodies (MAbs) such as MAbs specific for human MIF.

The preferred chromatographic methods are immunoaffinity chromatography, ion exchange chromatography with carriers bearing sulfopropyl groups and reversed phase high performance liquid chromatography (HPLC).

The compounds of the invention are isolated by the usual techniques, for example filtration or ultrafiltration, dialysis, dissolution and reprecipitation in suitable salt or buffer solutions and solvent mixtures, solvent evaporation, lyophilization, and the like.

Mutants of the invention are formed by spontaneous or chemically induced mutations at the DNA level or by replacement of amino acids by chemical synthesis.

Fragments of the invention are formed by spontaneous or chemically induced mutations at the DNA level, whereby a triplet coding for an amino acid is changed to a stop codon, or at the peptide level by cleaving bonds chemically or enzymatically. Suitable enzymes for the preparation of fragments of the invention are for example proteases. For instance, papain, trypsin, α-chymotrypsin, thermolysin, pepsin, subtilisin, endoproteinase Lys-C from *Lysobacter enzymogenes*, V8 protease from *Staphylococcus aureus* or related proteases may be added to a solution of a polypeptide of the invention, and the resulting mixture of fragments may be separated by chromatographic methods, e.g. by gel filtration and/or reversed phase HPLC.

Extracts, cell supernatants and culture filtrates of genetically engineered microorganisms or continuous mammalian cell lines containing recombinant polypeptides of the invention or derivatives thereof according to the invention are obtained by recombinant DNA techniques and pre-purified as discussed above. In particular, polypeptides and derivatives thereof according to the invention can be prepared by culturing transformed host cells expressing polypeptides of the invention or derivatives thereof under conditions which allow expression of heterologous polypeptides, and when required, isolating the desired compounds and/or converting them into derivatives thereof. The steps involved in the preparation of the polypeptides and derivatives of the invention by recombinant DNA techniques will be discussed in more detail hereinbelow.

In another embodiment of the invention, the polypeptides and derivatives thereof according to the invention, particularly fragments, are synthesized by chemical methods, e.g. by condensation reactions as described for example by M. Bodanszky, "Principles of Peptide Synthesis" (Springer 1984). Fragments are synthesized e.g. by a solid-phase method, wherein an N-protected amino acid is coupled to a suitable resin, the protecting group is removed, a second N-protected amino acid is condensed with the amino group of the first amino acid, the cycle of deprotection/condensation with further N-protected amino acids is repeated until the peptide residue of the desired compound is complete, and finally this peptide residue is cleaved from the resin and deprotected. Similarly short N-protected oligopeptides may be used in place of single N-protected amino acids. Suitable resins, protecting groups, condensation reagents and reaction conditions are well known in the art.

The invention relates also to DNAs coding for a polypeptide of the invention or for derivatives thereof, to mutants of such DNAs, e.g. DNAs wherein one or more, especially one, two, three or four, nucleotides are mutated, and to fragments of such DNAs comprising at least 15 nucleotides.

By definition, such DNAs comprise coding single-stranded DNAs, double-stranded DNAs consisting of said coding DNAs and of complementary DNAs thereto, or these complementary (single-stranded) DNAs themselves.

In particular, the invention concerns a DNA coding for MRP-160 of the nucleotide sequence given in FIGS. 1(A–J) and mutants and fragments of such a DNA.

In particular, the invention concerns a DNA fragment which comprises nucleotides 2765 to 4414 of a DNA of the nucleotide sequence given in FIGS. 1(A–J).

The invention also concerns DNAs which hybridize with a DNA, mutant or fragment thereof according to the invention.

Furthermore, the invention concerns DNAs, mutants or fragments thereof according to the invention which are of genomic origin.

The DNAs of the invention can be prepared for example by culturing a transformed host and, when required, isolating the desired DNA therefrom, or by chemical synthesis through nucleotide condensation.

In particular, such DNAs can be prepared by
a) isolating mRNA from suitable cells, for example human mononuclear leukocytes or human embryonic epithelial lung cells, selecting the desired mRNA, e.g. by hybridization with a DNA probe or by expression in a suitable expression system and screening for expression of the desired polypeptide, preparing single-stranded cDNA complementary to that mRNA, then double-stranded cDNA therefrom, or
b) isolating cDNA from a cDNA library and selecting the desired cDNA, e.g. using a DNA probe or using a suitable expression system and screening for expression of the desired polypeptide, or
c) isolating genomic DNA from suitable human tissue, e.g. placenta or fetal liver cells, and selecting the desired DNA, e.g. using a DNA probe or using a suitable expression system and screening for expression of the desired polypeptide, and
d) incorporating the double-stranded DNA of step a), b) or c) into an appropriate expression vector,
e) transforming appropriate host cells with the obtained hybrid vector,
f) selecting transformed host cells which contain the desired DNA from untransformed host cells, and, when required,
g) isolating the desired DNA and/or converting the DNA into a mutant or fragment thereof.

Polyadenylated messenger RNA (step a) is isolated from the suitable cells, e.g. human mononuclear leukocytes or human embryonic epithelial lung cells, by known methods. For example, the leukocytes may be derived from fresh human blood, e.g. from buffy coats consisting of white blood cells, or from leukocytes of an established continuous cell line which can be expanded in culture. Isolation methods involve, for example, homogenizing stimulated leukocytes in the presence of a detergent and a ribonuclease inhibitor, e.g. heparin, guanidinium isothiocyanate or mercaptoethanol, extracting the mRNA with suitable chloroform-phenol mixtures, optionally in the presence of salt and buffer solutions, detergents and/or cation chelating agents, and precipitating mRNA from the remaining aqueous, salt-containing phase with ethanol, isopropanol or the like. The isolated mRNA may be further purified by centrifuging in a cesium chloride gradient followed by ethanol precipitation and/or by chromatographic methods, e.g. affinity chromatography, for example chromatography on oligo(dT) cellulose or on oligo(U) sepharose. Preferably, such purified total mRNA is fractionated according to size by gradient centrifugation, e.g. in a linear sucrose gradient, or chromatography on suitable size fractionation columns, e.g. on agarose gels.

The desired mRNA is selected by screening the mRNA directly with a DNA probe, or by translation in suitable cells or cell-free systems and screening the obtained polypeptides.

The selection of the desired mRNA is preferably achieved using a DNA hybridization probe, thereby avoiding the additional step of translation. Suitable DNA probes are DNAs of known nucleotide sequence consisting of at least 17 nucleotides, for example synthetic DNAs, cDNAs derived from mRNA coding for the desired polypeptides in an animal species whose DNA exhibits sequence homologies with human DNA, or genomic DNA fragments comprising e.g. adjacent DNA sequences which are isolated from a natural source or from a genetically engineered microorganism.

Synthetic DNA probes are synthesized according to known methods as detailed hereinbelow, preferably by stepwise condensation using the solid phase phosphotriester, phosphite triester or phosphoramidite method, e.g. the condensation of dinucleotide coupling units by the phosphotriester method. These methods are adapted to the synthesis of mixtures of the desired oligonucleotides by using mixtures of two, three or four nucleotides dA, dC, dG and/or dT in protected form or the corresponding dinucleotide coupling units in the appropriate condensation step as described by Y. Ike et al. (Nucleic Acids Research 11, 477, 1983).

For hybridization, the DNA probes are labelled, e.g. radioactively labelled by the well known kinase reaction. The hybridization of the size-fractionated mRNA with the DNA probes containing a label is performed according to known procedures, i.e. in buffer and salt solutions containing adjuncts, e.g. calcium chelators, viscosity regulating compounds, proteins, irrelevant DNA and the like, at temperatures favoring selective hybridization, e.g. between 0° C. and 80° C., for example between 25° C. and 50° C. or around 65° C., preferably at around 20° lower than the hybrid double-stranded DNA melting temperature.

Fractionated mRNA may be translated in cells, e.g. frog oocytes, or in cell-free systems, e.g. in reticulocyte lysates or wheat germ extracts. The obtained polypeptides are screened for mediator activity or for reaction with antibodies raised against the native mediator, e.g. in an immunoassay, for example radioimmunoassay, enzyme immunoassay or immunoassay with fluorescent markers. Such immunoassays and the preparation of polyclonal and monoclonal antibodies are well known in the art and are applied accordingly.

The preparation of a single-stranded complementary DNA (cDNA) from the selected mRNA template is well known in the art, as is the preparation of a double-stranded DNA from a single-stranded DNA. The mRNA template is incubated with a mixture of deoxynucleoside triphosphates, optionally radioactively labelled deoxynucleoside triphosphates (in order to be able to screen the result of the reaction), a primer sequence such as an oligo-dT residue hybridizing with the poly(A) tail of the mRNA and a suitable enzyme such as a reverse transcriptase e.g. from avian myeloblastosis virus (AMV). After degradation of the template mRNA e.g. by alkaline hydrolysis, the cDNA is incubated with a mixture of deoxynucleoside triphosphates and a suitable enzyme to give a double-stranded DNA. Suitable enzymes are for instance a reverse transcriptase, the Klenow fragment of E. coli DNA polymerase I or T4 DNA polymerase. Usually, a hairpin loop structure formed spontaneously by the single-stranded cDNA acts as a primer for the synthesis of the second strand. This hairpin structure is removed by digestion with S1 nuclease. Alternatively, the 3'-end of the single-stranded DNA is first extended by homopolymeric deoxynucleotide tails prior to the hydrolysis of the mRNA template and the subsequent synthesis of the second cDNA strand.

In the alternative, double-stranded cDNA is isolated from a cDNA library and screened for the desired cDNA (step b). The cDNA library is constructed by isolating mRNA from suitable cells, e.g. human mononuclear leukocytes or human embryonic epithelial lung cells, and preparing single-stranded and double-stranded cDNA therefrom as described above. This cDNA is digested with suitable restriction endonucleases and incorporated into λ phage, e.g. λ charon 4A or λ gt11 following established procedures. The cDNA library replicated on nitrocellulose membranes is screened by using a DNA probe as described hereinbefore, or expressed in a suitable expression system and the obtained polypeptides screened for reaction with an antibody specific for the desired compounds, e.g. an antibody specific for human MIF.

As a further alternative, genomic DNA may be isolated and screened for the desired DNA (step c). Genomic DNA is isolated from suitable human tissue, preferably from human placenta or human fetal liver cells, according to methods known in the art. A genomic DNA library is prepared therefrom by digestion with suitable restriction endonucleases, e.g. AluI and HaeIII, and incorporation into λ phage, e.g. λ charon 4A or λ gt11, following established procedures. The genomic DNA library replicated on nitrocellulose membranes is screened with a DNA probe as described hereinbefore, or expressed in a suitable expression system and the obtained polypeptides screened as described hereinbefore.

A variety of methods are known in the art for the incorporation of double-stranded cDNA or genomic DNA into an appropriate vector (step d). For example, complementary homopolymer tracts may be added to the double-stranded DNA and the vector DNA by incubation in the presence of the corresponding deoxynucleoside triphosphates and an enzyme such as terminal deoxynucleotidyl transferase. The vector and double-stranded DNA are then joined by base pairing between the complementary homopolymeric tails and finally ligated by specific joining enzymes such as ligases. Other possiblities are the addition of synthetic linkers to the termini of the double-stranded DNA, or the incorporation of the double-stranded DNA into the vector by blunt- or staggered-end ligation. Appropriate vectors will be discussed in detail hereinbelow.

The transformation of appropriate host cells with the obtained hybrid vector (step e) and the selection of transformed host cells (step f) are well known in the art and are described in detail further below. Hybrid vectors and host cells may be particularly suitable for the production of DNA, or else for the production of the desired polypeptides.

The isolation of the desired DNA, mutants and fragments therof according to the invention is achieved by methods known in the art, e.g. extraction with phenol and/or chloroform. Optionally, the DNA can be further manipulated e.g. by treatment with mutagenic agents to obtain mutants, or by digestion with restriction enzymes to obtain fragments, modify one or both termini to facilitate incorporation into the vector, remove intervening sequences and the like.

The nucleotide sequence of a DNA according to the invention can be determined by methods known per se, for example by the Maxam-Gilbert method using end-labelled DNA or by the dideoxy chain termination method of Sanger.

The preparation of a DNA, mutant or derivative thereof according to the invention may also be performed by means of chemical synthesis. Suitable methods for the synthesis of DNA have been presented in summary form by S. A. Narang (Tetrahedron 39, 3, 1983). The known synthesis techniques allow the preparation of polynucleotides up to 40 bases in length, in good yield, high purity and in a relatively short time. Suitably protected nucleotides are linked with one another by the phosphodiester method (K. L. Agarwal et al., Angew. Chemie 84, 489, 1972), the more efficient phosphotriester method (C. B. Reese, Tetrahedron 34, 3143, 1972), the phosphite triester method (R. L. Letsinger et al., J. Am. Chem. Soc. 98, 3655, 1976) or phosphoramidite method (S. L. Beaucage and M. H. Carruthers, Tetrahedron 22, 1859, 1981). Simplification of the synthesis of the oligonucleotides and polynucleotides is made possible by the solid phase method, in wich the nucleotide chains are bound to a suitable polymer. H. Rink et al. (Nucl. Acids Research 12, 6369, 1984) use trinucleotides instead of individual nucleotides and link them by the phosphotriester method in the solid phase synthesis. A polynucleotide with up to 67 bases can thus be prepared in a short time and with good yields. The actual double-stranded DNA is built up enzymatically from chemically prepared overlapping oligonucleotides from both DNA strands, which are held together in the correct arrangement by base-pairing and are then chemically linked by the enzyme DNA ligase. Another possibility comprises incubating overlapping single oligonucleotides from the two DNA strands in the presence of the four required deoxynucleoside triphosphates with a DNA polymerase, for example DNA polymerase I, the Klenow fragment of polymerase I or T4 DNA polymerase, or with AMV (avian myeloblastosis virus) reverse transcriptase. The two oligonucleotides are thereby held together in the correct arrangement by base-pairing and are supplemented with the required nucleotides by the enzyme to give a complete double-stranded DNA (S. A. Narang et al., Anal. Biochem. 121, 356, 1982).

The invention further concerns hybrid vectors comprising a DNA, mutant or fragment thereof as defined hereinbefore coding for a polypeptide or a derivative according to the invention operatively linked to expression control sequences. Particularly preferred are hybrid vectors comprising a DNA of FIGS. 1(A–J), a mutant or derivative thereof, or a DNA fragment consisting of the nucleotides 2765 to 4414 of a DNA of FIGS. 1(A–J), operatively linked to expression control sequences.

The hybrid vectors of the invention provide for replication and expression of the desired DNA in a suitable host, either as an extrachromosomal element or by integration in the host chromosome. Several possible vector systems are available for integration and expression of the cloned DNA of the invention. In principle, all vectors which replicate and express the desired polypeptide gene according to the invention in the chosen host are suitable. The vector is selected depending on the host cells envisaged for transformation. In general, such host cells may be prokaryotic or eukaryotic microorganisms such as bacteria or yeasts, or cells of higher eukaryotic origin such as vertebrate, in particular mammalian, cells. Suitable host cells will be discussed in detail hereinbelow. In principle, the hybrid vectors of the invention comprise the DNA as defined hereinbefore, an origin of replication or an autonomously replicating sequence, dominant marker sequences, expression control sequences essential for the transcription and translation of the desired DNA and, optionally, signal sequences and additional restriction sites.

An origin of replication or an autonomously replicating sequence (a DNA element which confers autonomously replicating capabilities to extrachromosomal elements) is provided either by construction of the vector to include an exogeneous origin such as derived from Simian virus (SV 40) or another viral source, or by the host cell chromosomal mechanisms.

The markers allow for selection of host cells which contain the vector. Selection markers include genes which confer resistance to heavy metals such as copper or to antibiotics such as tetracycline, ampicillin, geneticin (G-418) or hygromycin, or genes which complement a genetic lesion of the host cells such as the absence of thymidin kinase, hypoxanthine phosphoryl transferase, dihydrofolate reductase, or the like.

As expression control sequences, the vector DNA comprises a promoter, i.e. a DNA sequence which directs RNA polymerase to bind to DNA and to initiate RNA synthesis, ribosomal binding sites, i.e. sequences necessary for the initiation of translation, transcription and translation termination signals and sequences necessary for stabilizing the mRNA, and, optionally, enhancers and further regulatory sequences.

A wide variety of promoting sequences may be employed, depending on the nature of the host cell. Promoters that are strong and at the same time well regulated are the most useful. Sequences for the initiation of translation are for example Shine-Dalgarno sequences. Sequences necessary for the initiation and termination of transcription and for stabilizing the mRNA are commonly available from the noncoding 5'-regions and 3'-regions, respectively, of viral or eukaryotic cDNAs, e.g. from the expression host Enhancers are transcription-stimulating DNA sequences of viral origin, e.g. derived from Simian virus, polyoma virus, bovine papilloma virus or Moloney sarcoma virus, or of genomic origin.

Signal sequences may be, for example, a presequence or secretory leader directing the secretion of the polypeptide, splice signals, or the like.

The various DNA segments of the vector DNA are operationally linked, i.e. they are contiguous and placed into a functional relationship with each other.

Examples of vectors which are suitable for replication and expression in an *E. coli* strain are bacteriophages, for example derivatives of λ bacteriophages, or plasmids, such as, in particular, the plasmid ColE1 and its derivatives, for example pMB9, pSF2124, pBR317 or pBR322 and plasmids derived from pBR322, such as pUC9, pUCK0, pHRi148 and pLc24. Suitable vectors contain a complete replicon, a marker gene, recognition sequences for restriction endonucleases, so that the foreign DNA and, if appropriate, the expression control sequence can be inserted at these sites, and optionally signal sequences and enhancers.

Microbial promoters are, for example, the strong leftward promoter $P_L$ of bacteriophage λ which is controlled by a temperature sensitive repressor. Also suitable are *E. coli* promoters such as the lac (lactose) promoter regulated by the lac repressor and induced by isopropyl-β-D-thiogalactoside, the trp (tryptophan) promoter regulated by the trp repressor and induced e.g. by tryptophan starvation, and the tac (hybrid trp-lac promoter) regulated by the lac repressor. Preferred are vectors which contain the $P_L$ promoter of bacteriophage λ.

Vectors which are suitable for replication and expression in yeast contain a yeast replication start and a selective genetic marker for yeast. One group of such vectors includes so-called ars sequences (autonomous replication sequences) as origin of replication. These vectors are retained extrachromosomally within the yeast cell after the transformation and are replicated autonomously. Furthermore, vectors which contain all or part of the 2μ (2 mikron) plasmid DNA from *Saccharomyces cerevisiae* can be used. Such vectors will get integrated by recombination into 2μ plasmids already existing within the cell, or replicate autonomously. 2μ sequences are particularly suitable when high transformation frequency and high copy numbers are to be achieved.

Expression control sequences which are suitable for expression in yeast are, for example, those of highly expressed yeast genes. Thus, the promoters for the TRP1 gene, the ADHI or ADHII gene, acid phosphatase (PHO3 or PHO5) gene, isocytochrome gene or a promoter involved with the glycolytic pathway, such as the promoter of the enolase, glyceraldehyde-3-phosphate kinase (PGK), hexokinase, pyruvate decarboxylase, phosphofructokinase, glucose-6-phosphate isomerase, 3-phosphoglycerate mutase, pyruvate kinase, triosephosphate isomerase, phosphoglucose isomerase and glucokinase genes, can be used.

Vectors suitable for replication and expression in mammalian cells are preferably provided with promoting sequences derived from DNA of viral origin, e.g. from Simian virus 40 (SV40), Rous sarcoma virus (RSV), adenovirus 2, bovine papilloma virus (BPV), papovavirus BK mutant (BKV), or mouse or human cytomegalovirus (CMV). Alternatively, the vectors may comprise promoters from mammalian expression products, such as actin, collagen, myosin etc., or the native promoter and control sequences which are normally associated with the desired gene sequence. For example, the plasmid may contain the enhancer unit of the mouse or human cytomegalovirus major immediate-early gene, the SV40 enhancer combined with the human α-globin promoter, and/or in addition inducible promoters, such as the ones derived from the heat shock or metallothionein genes. Preferred are vectors which contain the murine cytomegalovirus promoter.

Preferred hybrid vectors of the invention are hybrid vectors derived from the plasmid pUCK0 or from the plasmid $pP_L$mu-bio. Also preferred are the vectors designated pMRP160, pMRP160$_{ex}$ and pMRP70$_{PL}$.

Furthermore, the invention concerns transformed host cells expressing the polypeptides and derivatives of the invention, in particular host cells transformed with a hybrid vector according to the invention. Such host cells are genetically stable and can be activated from deep-frozen cultures by thawing and re-cloning.

Examples of suitable hosts are microorganisms which are devoid of or poor in restriction enzymes or modification enzymes, such as bacteria, in particular strains of *Escherichia coli*, for example *E. coli* X1776, *E. coli* Y1090, *E. coli* HB 101, *E. coli* W3110, *E. coli* HB101 /LM1035, *E. coli* JA 221, *E. coli* DH5α or *E. coli* K12 strain, *Bacillus subtilis, Bacillus stearothermophilus*, Pseudomonas, Haemophilus, Streptococcus and others, and yeasts, for example *Saccharomyces cerevisiae* such as *S. cerevisiae* GRF 18. Further suitable host cells are cells of higher organisms, in particular established continuous human or animal cell lines, e.g. human embryonic lung fibroblasts L132, human malignant melanoma Bowes cells, HeLa cells, SV40 virus transformed kidney cells of African green monkey COS-7 or Chinese hamster ovary (CHO) cells.

The above mentioned strains of *E. coli*, in particular *E. coli* K12, and Chinese hamster ovary (CHO) cells are preferred as hosts.

The invention also concerns processes for the preparation of transformed host cells wherein a suitable host cell as described hereinbefore is transformed with a hybrid vector according to the invention, and the transformed cells are selected.

Transformation of microorganisms is carried out as described in the literature, for example for *S. cerevisiae* (A. Hinnen et al., Proc.Natl.Acad.Sci.USA, 75, 1929,1978), for *B. subtilis* (Anagnostopoulos et al., J. Bacteriol. 81, 741, 1961), and for *E. coli* (M. Mandel et al., J. Mol. Biol. 53, 159, 1970).

Accordingly, the transformation procedure of *E. coli* cells includes, for example, $Ca^{2+}$ pretreatment of the cells so as to allow DNA uptake, and incubation with the hybrid vector. The subsequent selection of the transformed cells can be achieved, for example, by transferring the cells to a selective growth medium which allows separation of the transformed cells from the parent cells dependent on the nature of the marker sequence of the vector DNA. Preferably, a growth medium is used which does not allow growth of cells which do not contain the vector. The transformation of yeast comprises, for example, steps of enzymatic removal of the yeast cell wall by means of glucosidases, treatment of the obtained spheroplasts with the vector in the presence of polyethylene glycol and $Ca^{2+}$ ions, and regeneration of the cell wall by embedding the spheroplasts into agar. Preferably, the regeneration agar is prepared in a way to allow regeneration and selection of the transformed cells as described above at the same time.

Transformation of cells of higher eukaryotic origin, such as mammalian cell lines, is preferably achieved by transfection. Transfection is carried out by conventional techniques, such as calcium phosphate precipitation, microinjection, protoplast fusion, electroporation, i.e. introduction of DNA by a short electrical pulse which transiently increases the permeability of the cell membrane, or in the presence of helper compounds such as diethylaminoethyldextran, dimethyl sulfoxide, glycerol or polyethylene glycol, and the like. After the transfection procedure, transfected cells are identified and selected e.g. by cultivation in a selective medium chosen depending on the nature of the selection marker, for example standard culture media such as Dulbecco's modified Eagle medium (DMEM), minimum essential medium, RPMI 1640 medium and the like, containing e.g. the corresponding antibiotic.

The transformed host cells are cultured by methods known in the art in a liquid medium containing assimilable sources of carbon, e.g. carbohydrates such as glucose or lactose, nitrogen, e.g. amino acids, peptides, proteins or their degradation products such as peptones, ammonium salts or the like, and inorganic salts, e.g. sulfates, phosphates and/or carbonates of sodium, potassium, magnesium and calcium. The medium furthermore contains, for example, growth-promoting substances, such as trace elements, for example iron, zinc, manganese and the like.

The medium is preferably so chosen as to exert a selection pressure and prevent the growth of cells which have not been transformed or have lost the hybrid vector. Thus, for example, an antibiotic is added to the medium if the hybrid vector contains an antibiotic resistance gene as marker. If, for instance, a host cell is used which is auxotrophic in an essential amino acid whereas the hybrid vector contains a gene coding for an enzyme which complements the host defect, a minimal medium deficient of said amino acid is used to culture the transformed cells.

Cells of higher eukaryotic origin such as mammalian cells are grown under tissue culture conditions using commercially available media, for example Dulbecco's modified Eagle medium (DMEM), minimum essential medium, RPMI 1640 medium and the like as mentioned above, optionally supplemented with growth-promoting substances and/or mammalian sera. Techniques for cell cultivation under tissue culture condition are well known in the art and include homogeneous suspension culture, e.g. in an airlift reactor or in a continuous stirrer reactor, or immobilized or entrapped cell culture, e.g. in hollow fibres, microcapsules, on agarose microbeads, porous glass beads, ceramic cartridges, or other microcarriers.

Culturing is effected by processes which are known in the art. The culture conditions, such as temperature, pH value of the medium and fermentation time, are chosen so that a maximum titer of the polypeptide or derivative of the invention is obtained. Thus, an E. coli or yeast strain is preferably cultured under aerobic conditions by submerged culture with shaking or stirring at a temperature of about 20° C. to 40° C., preferably at about 30° C., and a pH value of 4 to 8, preferably of about pH 7, for about 4 to 30 hours, preferably until maximum yields of the polypeptide or derivative of the invention are reached.

When the cell density has reached a sufficient value, the culture is interrupted and the polypeptide or derivative can be isolated. If the hybrid vector contains a suitable secretion signal sequence, the polypeptide or derivative is excreted by the transformed cell directly into the culture medium. Otherwise, the cells have to be destroyed, for example by treatment with a detergent such as SDS, NP-40, Triton or deoxycholic acid, lysed with lysozyme or a similarly acting enzyme, or disrupted by ultra-sound. If yeast is used as a host microorganism, the cell wall may be removed by enzymatic digestion with a glucosidase. Alternatively or additionally, mechanical forces, such as shearing forces (e.g. French press, Dyno mill and the like) or shaking with glass beads or aluminium oxide, or alternating freezing, for example in liquid nitrogen, and thawing, for example at 30° C. to 40° C., as well as ultra-sound can be used to break the cells.

The cell supernatant or the solution obtained after centrifugation of the mixture obtained after breaking the cells, which contains proteins, nucleic acids and other cell constituents, is enriched in proteins, including the polypeptides of the invention, in a manner which is known per se. Thus, for example, most of the non-protein constituents are removed by polyethyleneimine treatment and the proteins including the polypeptides and derivatives of the invention are precipitated, for example, by saturation of the solution with ammonium sulfate or with other salts. Otherwise, the cell supernatant or lysate is directly pre-purified using chromatographic methods as described hereinbefore.

The polypeptides and derivatives thereof according to the invention are useful for gaining a better understanding of the role of the mononuclear phagocyte system, that is to say to define the lymphokine signal and the nature of the cellular response to it in macrophage populations.

Due to their inflammation mediator activity, the polypeptides and derivatives thereof according to the invention can be used to influence inflammatory processes. They are therefore useful for therapy of chronic inflammatory conditions.

In addition, the polypeptides or derivatives according to the invention are useful for the study, identification and production of antagonists which can be used as anti-inflammatory drugs.

The invention also concerns pharmaceutical compositions comprising a therapeutically effective amount of a polypeptide or a derivative of the invention and a pharmaceutically acceptable carrier, e.g. an inorganic or organic, solid or liquid carrier.

The pharmaceutical compositions according to the invention are those for enteral, e.g. rectal or oral, administration and preferably for parenteral, e.g. intranasal, intramuscular, subcutaneous or intravenous, administration to warm-blooded animals including man. Depending on the intended method of administration, the pharmaceutical compositions may be in unit dose form, for example in ampoules, vials, suppositories, dragées, tablets, capsules or nasal sprays in liquid or solid form.

The amount of the therapeutically effective compound to be administered depends on the condition of the patient, such as the body weight, the nature and severity of the disease and the general condition and also on the mode of administration, and is carried out in accordance with the assessment of the physician giving the treatment. The effective dose of a polypeptide of the invention or a derivative thereof is in the order of magnitude of from 0.001 to 1 $\mu$g per kg body weight per day.

The pharmaceutical compositions according to the invention contain the customary inorganic or organic, solid or liquid pharmaceutically acceptable carriers, optionally together with other therapeutically effective compounds and/or adjuncts. There are preferably used solutions or suspensions of the active ingredient, especially isotonic aqueous solutions or suspensions, or also lyophilized preparations which are dissolved in water shortly before use. The pharmaceutical compositions may be sterilized and/or contain preservatives, stabilizers, wetting agents, emulsifiers, solubilizers, viscosity-increasing substances, salts for regulating the osmotic pressure and/or buffers, and also other proteins, for example human serum albumin or human blood plasma preparations.

Preferred are pharmaceutical compositions in the form of liposomes in aqueous dispersion containing a therapeutically effective amount of a polypeptide or derivative thereof. There are suitable, in particular, liposomes having a population of as homogeneous a size as possible and a diameter of approximately from $0.2 \times 10^{-8}$ to $5.0 \times 10^{-6}$ m consisting of one or more double layers of lipid components, for example amphipatic lipids such as phospholipids like lecithin, cephalin or phosphatidic acid, and optionally neutral lipids, for example cholesterol, enclosing an aqueous interior containing a polypeptide or derivative of the invention. Preferred are liposomes consisting of a mixture of synthetic phosphatidylserine and phosphatidylcholine.

The invention further concerns polyclonal and monoclonal antibodies specific for the polypeptides of the invention, or for derivatives according to the invention, in particular antibodies specific for MRP-160, for rMRP-70, or for fragments of MRP-160, or derivatives of such antibodies which retain the specificity of the antibody from which they are derived.

Polyclonal antibodies of the invention are of mammalian origin, e.g. mouse, rat, rabbit, donkey, goat, sheep, equine, pig, chimpanzee or human origin, or of avian origin, e.g. chicken. Preferred are mouse, rat, rabbit, goat, sheep or chicken antibodies, in particular rabbit antibodies, or their derivatives. Preferred polyclonal antibodies are specific for MRP-160, for rMRP-70 or for fragments of MRP-160 comprising between 12 and 30 consecutive amino acids of FIGS. 1(A–J). Particularly preferred are polyclonal antibodies specific for MRP- 160, for rMRP-70, or for the fragments of MRP-160 corresponding to amino acids 1189-1204, 1242-1255, 1409-1427, and 162-177, respectively, of FIGS. 1(A–J). Most preferred are polyclonal rabbit antibodies specific for rMRP-70.

Preferred are monoclonal antibodies specific for the polypeptides of the invention or for derivatives according to the invention, in particular monoclonal antibodies specific for MRP-160 or for rMRP-70, or for fragments of MRP-160, or derivatives of such antibodies. Monoclonal antibodies of the invention are of mammalian origin, e.g. mouse, rat or human origin, preferably mouse origin. Preferred are monoclonal mouse antibodies specific for rMRP-70.

The specificity of an antibody towards a polypeptide or derivative of the invention can be detected qualitatively in an enzyme immunoassay wherein the wells of a microtiter plate are coated with the polypeptide, then treated with the antibody to be tested, and bound antibody is detected with labelled antiserum directed against the antibody. For example, the specificity of a mouse monoclonal antibody of the invention is determined in a sandwich type enzyme immunoassay wherein the wells of a microtiter plate are coated with a rabbit polyclonal antibody specific for a polypeptide of the invention, followed by the polypeptide itself, then treated with the antibody to be tested, and bound monoclonal antibody is detected with labelled antiserum directed against the constant part of mouse antibodies.

Derivatives of an antibody of the invention retain the specificity of the antibody from which they are derived, i.e. they retain the characteristic binding pattern of the parent antibody. Examples of such derivatives are antibody fragments, conjugates of the antibodies with an enzyme, a fluorescent marker, a chemiluminescent marker, a metal chelate, paramagnetic particles, avidin, biotin or the like, or radioactively labelled antibodies.

Antibody fragments of the invention are for example the univalent fragments Fab or Fab' or the divalent fragment F(ab')$_2$.

Enzymes used for antibody conjugates of the invention are, for example, horseradish peroxidase, alkaline phosphatase, β-D-galactosidase, glucose oxidase, glucoamylase, carbonic anhydrase, acetylcholinesterase, lysozyme, malate dehydrogenase or glucose-6-phosphate dehydrogenase.

Fluorescent markers conjugated with antibodies of the invention can be fluorescein, fluorochrome, rhodamine, and the like.

Chemiluminescence markers are e.g. acridinium esters of luminol.

In such conjugates, the antibody is bound to the conjugation partner directly or by way of a spacer or linker group.

Examples of metal chelators are ethylenediaminetetraacetic acid (EDTA), diethylenetriaminepentaacetic acid (DPTA), 1,4,8,11-tetraazatetradecane, 1,4,8,11-tetraazatetradecane-1,4,8,11 -tetraacetic acid, 1 -oxa-4,7,12,15-tetraazaheptadecane-4,7,12,1 5-tetraacetic acid, or the like.

Radioactively labelled antibodies of the invention contain e.g. radioactive iodine ($^{123}$I, $^{125}$I,), tritium ($^3$H), carbon ($^{14}$C), sulfur ($^{35}$S), yttrium ($^{90}$Y), technetium ($^{99m}$Tc), or the like.

Polyclonal antibodies of the invention and derivatives thereof are obtained by processes known per se, for example by a process wherein a suitable mammal or bird is immunized with a polypeptide or derivative thereof according to the invention such as MRP-160, rMRP-70 or fragments of MRP-160, optionally in the presence of an adjuvant, the blood serum of the immunized mammal or eggs of the immunized bird are collected and, when required, the antibodies are isolated and/or converted into derivatives thereof.

Suitable mammals are those which recognize the antigen, i.e. the polypeptide or derivative thereof according to the invention, as a foreign molecule, for example mice, rats, rabbits, donkeys, goats, sheep, pigs or horses. Suitable birds are chicken.

The routes of immunization include, among others, intradermal, subcutaneous, intramuscular, intraperitoneal, intravascular and intracranial injections. Since high antibody titers are desired, a series of injections is commonly given. The immunization is, for example, performed by injecting the antigen two, three, four or more times parenterally, e.g. intraperitoneally and/or subcutaneously, in regular or irregular intervals of a few days, e.g. three to seven days, up to several months, for example four weeks.

The antigen may be mixed with adjuvants, i.e. agents which will further increase the immune response, for the immunization procedure. Possible adjuvants are Freund's complete adjuvant (emulsion of mineral oil, water, and mycobacterial extracts), Freund's incomplete adjuvant (emulsion of water and oil only), aluminium hydroxide gels etc.

The immune response of the mammal is preferably monitored by a suitable antibody assay, e.g. an enzyme immunoassay as described hereinbefore. The blood of the mammal is collected a few, e.g. two to five, days after the last injection. Likewise, the immune response of the bird is monitored by analyzing eggs layed a few weeks, e.g. four to six weeks, after the last injection. The antibodies are isolated by known methods. They are first concentrated, e.g. by precipitation with ammonium sulfate, dialysis against hygroscopic material such as polyethylene glycol (PEG), filtration through selective membranes, or the like, and, if necessary and/or desired, the concentrated antibodies are purified by the customary chromatography methods, e.g. hydroxylapatite chromatography, immunoaffinity chromatography, gel filtration, ion exchange chromatography, or chromatography over DEAE cellulose or protein A.

Fragments of the antibodies, for example Fab, Fab' or F(ab')$_2$ fragments, can be obtained from the antibodies prepared as described above by methods known per se, e.g. by digestion with enzymes such as papain or pepsin and/or cleavage of disulfide bonds by chemical reduction.

Conjugates of antibodies of the invention are prepared by methods known in the art, e.g. by reacting an antibody prepared as described above in the presence of a coupling agent, e.g. glutaraldehyde, periodate, N,N'-o-phenylenedimaleimide, N-(m-maleimidobenzoyloxy)-succinimide, N-(3-[2'-pyridyldithio]-propionoxy)-succinimide, N-ethyl-N'-(3-dimethylaminopropyl)-carbodiimide or the like. Conjugates with biotin are prepared e.g. by reacting antibodies with an activated ester of biotin such as the biotin N-hydroxy-succinimide ester. Conjugates with fluorescent or chemiluminescent markers are prepared in the presence of a coupling agent, e.g. those listed above, or by reaction with an isothiocyanate, preferably fluorescein-isothiocyanate.

Antibodies radioactively labelled with iodine are obtained from the antibodies of the invention by iodination known per se, for example with radioactive sodium or potassium iodide and a chemical oxidizing agent, such as sodium hypochlorite, chloramine T or the like, or an enzymatic oxidizing agent, such as lactoperoxidase or glucose oxidase and glucose. Antibodies according to the invention are coupled to yttrium for example by diethylenetriaminepentaacetic acid (DPTA)-chelation. Technetium-99m labelled antibodies are prepared by ligand exchange processes, for example by reducing pertechnate ($TcO_4^-$) with stannous ion solution, chelating the reduced technetium onto a Sephadex column and applying the antibodies to this column, or by direct labelling techniques, e.g. by incubating pertechnate, a reducing agent such as $SnCl_2$, a buffer solution such as sodium-potassium phthalate solution, and the antibodies.

The monoclonal antibodies of the invention and derivatives thereof are obtained by processes known per se wherein cells of a hybridoma cell line secreting the desired monoclonal antibodies are multiplied in vitro or in vivo and, when required, the obtained monoclonal antibodies are isolated and/or converted into derivatives thereof.

Multiplication in vitro is carried out in suitable culture media, which are the customary standard culture media, for example Dulbecco's modified Eagle medium (DMEM) or RPMI 1640 medium, optionally replenished by a mammalian serum, e.g. fetal calf serum, or trace elements and growth sustaining supplements, e.g feeder cells such as normal mouse peritoneal exudate cells, spleen cells, bone marrow macrophages, 2-aminoethanol, insulin, transferrin, low density lipoprotein, oleic acid, or the like.

In vitro production provides relatively pure antibody preparations and allows scale-up to give large amounts of the desired antibodies. Techniques for mammalian cell cultivation under tissue culture conditions are known in the art and include homogeneous suspension culture, e.g. in an airlift reactor or in a continuous stirrer reactor, or immobilized or entrapped cell culture, e.g. in hollow fibres, microcapsules, on agarose microbeads or ceramic cartridges.

Large quantities of the desired monoclonal antibodies can also be obtained by multiplying the cells in vivo. For this purpose, hybridoma cells producing the desired antibodies are injected into histocompatible mammals to cause growth of antibody-producing tumors. Optionally, the animals are primed with a hydrocarbon, especially mineral oils such as pristane (tetramethyl pentadecane), prior to the injection. After one to three weeks, the antibodies are isolated from the body fluids of those mammals. For example, hybridoma cells derived from Balb/c mice that produce the desired monoclonal antibodies are injected intraperitoneally into Balb/c mice optionally pre-treated with pristane, and, after one to two weeks, ascitic fluid is taken from the animals.

Isolation, purification and derivatization of the monoclonal antibodies is carried out as described above for polyclonal antibodies. Radioactively labelled monoclonal antibodies may also be prepared by adding radioactively labelled nutrients to the culture media of the in vitro cultivation. Such labelled nutrients contain e.g. radioactive carbon.

The invention further concerns hybridoma cell lines which secrete the monoclonal antibodies of the invention.

In particular, the invention concerns hybridoma cell lines which are hybrids of myeloma cells and B lymphocytes of a mammal immunized with a polypeptide or derivative thereof according to the invention. Preferentially, these cell lines are hybrids of mouse myeloma cells and B lymphocytes of a syngeneic mouse immunized with rMRP-70.

The hybridoma cell lines of the invention are genetically stable, secrete monoclonal antibodies of the invention with constant specificity and may be kept in deep-frozen cultures and reactivated by thawing and optionally re-cloning.

The invention also concerns a process for the preparation of hybridoma cell lines secreting the monoclonal antibodies of the invention wherein a suitable mammal is immunized with a polypeptide or derivative thereof according to the invention, antibody producing cells of this mammal are fused with cells of a continuous cell line, the hybrid cells obtained in the fusion are cloned, and cell clones secreting the desired monoclonal antibodies are selected.

The immunization is performed as hereinbefore described for the preparation of polyclonal antibodies. Antibody-producing cells of the immunized mammals, preferably lymphoid cells such as spleen lymphocytes, taken for example one to five days after the final injection, are fused with the cells of a continuous cell line, i.e. a continuously replicating cell clone which confers this replication ability to the hybrid cells resulting from the fusion. An example for such a cell line is a tumor cell line (myeloma) which does not itself actually produce immunoglobulins or fragments thereof but has the potential to produce and secrete large amounts of antibody, and which carries a genetic marker so that the hybrid cells can be selected against non-fused parent cells. Several suitable myeloma cell lines are known in the art. Preferred are myeloma cell lines lacking the enzyme hypoxanthine guanine phosphoribosyl transferase (HGPRT) or the enzyme thymidine kinase (TK), which therefore do not survive in a selective culture medium containing hypoxanthine, aminopterin and thymidine (HAT medium). Particularly preferred are myeloma cells and derived cell lines that do not survive in HAT medium and do not secrete immunoglobulins or fragments thereof, such as the cell lines P3x63Ag8.653 or Sp2/0-Ag 14.

The fusion is performed in the presence of a fusion promoter, for example Sendai virus or other paramyxo viruses, optionally in UV-inactivated form, or chemical fusogens such as calcium ions, surface-active lipids, e.g. lysolecithin, or polyethylene glycol (PEG) Preferentially, the myeloma cells are fused with a three- to twentyfold excess of spleen cells from immunized mammals in a solution containing about 30% to about 60% of polyethylene glycol of a molecular weight between 1000 and 4000.

After the fusion, the cells are resuspended and cultivated in a selective medium chosen depending on the genetic selection marker, for example HAT medium. In this medium, only hybridoma cells will survive, because they combine the ability to grow and replicate in vitro like the parent myeloma cells and the missing HGPRT or TK genes essential for the survival in HAT medium inherited from the antibody-producing spleen cells of the immunized mammals.

Suitable culture media for the expansion of hybridoma cells are the standard culture media, such as Dulbecco's modified Eagle medium (DMEM), minimum essential medium, RPMI 1640 medium and the like, optionally replenished by a mammalian serum, e.g. 10 to 15% fetal calf serum. Preferentially, feeder cells, e.g. normal mouse peritoneal exudate cells, spleen cells, bone marrow macrophages or the like, are added at the beginning of cell growth immediately after the fusion step to nourish the hybridoma cells and support their growth, especially where cell densities are low, by providing growth factors and the like. If phagocytic cells such as macrophages or monocytes are used, they can perform a helpful service in cleaning up the debris of dead myeloma cells always found after aminopterin treatment. The culture media are supplemented with selective medium in order to prevent myeloma cells from overgrowing the hybridoma cells.

The hybridoma cell culture supernatants are screened for the desired monoclonal antibodies, preferentially with an enzyme immunoassay or a radioimmunoassay. Positive hybridoma cells are cloned, e.g. by limiting dilution or in soft agar, preferentially twice or more. Optionally, hybridoma cells are passaged through animals, e.g. mice, by intraperitoneal injection and harvesting of ascites, which stabilizes hybridomas and improves growth characteristics. The cloned cell lines may be frozen in a conventional manner.

The polyclonal and monoclonal antibodies of the invention or their derivatives are useful for the qualitative and quantitative determination of the polypeptides or derivatives thereof according to the invention. These polypeptides and derivatives are markers for inflammatory conditions and at the same time markers for Hodgkin lymphomas.

For instance, the antibodies or derivatives thereof can be used in any of the known immunoassays which rely on the binding interaction between the antigenic determinants of the polypeptides or derivatives of the invention or the Hodgkin lymphoma markers and the paratopes of the antibodies. Examples of such assays are enzyme, radio-, fluorescence, chemiluminescence, immunoprecipitation, latex agglutination, hemagglutination immunoassays and immunostaining.

The antibodies according to the invention can be used as such or in the form of enzyme-conjugated derivatives in an enzyme immunoassay. Any of the known modifications of an enzyme immunoassay can be used, for example soluble phase (homogeneous) enzyme immunoassay, solid phase (heterogeneous) enzyme immunoassay, single enzyme immunoassay or double (sandwich) enzyme immunoassay with direct or indirect (competitive) determination of the polypeptides or derivatives of the invention.

An example of such an enzyme immunoassay is a sandwich enzyme immunoassay in which a suitable carrier, for example the plastic surface of a microtiter plate or of a test tube, e.g. of polystyrene, polypropylene or polyvinylchloride, glass or plastic beads, filter paper, dextran etc. cellulose acetate or nitrocellulose sheets, magnetic particles or the like, is coated with a polyclonal or monoclonal antibody of the invention by simple adsorption or optionally after activation of the carrier, for example with glutaraldehyde or cyanogen bromide. Then test solutions containing the polypeptides or derivatives of the invention or Hodgkin lymphoma markers and finally polyclonal antibodies which also react with the antigen and which are enzyme labelled, e.g. conjugated with alkaline phosphatase or horseradish peroxidase, are added. The amount of the polypeptides or derivatives thereof according to the invention or of Hodgkin lymphoma markers in the test solution is directly proportional to the amount of bound polyclonal antibodies and is determined by adding an enzyme substrate solution. The enzyme substrate reaction results, for example, in a color change which can be observed by eye or with optical measuring devices. The enzyme labelled polyclonal antibodies can be replaced by enzyme labelled monoclonal antibodies of the invention which recognize a different epitope of the antigen than the carrier-bound antibodies.

The antibodies according to the invention can be used as such or in the form of radioactively labelled derivatives in a radioimmunoassay (RIA). As described above for enzyme immunoassays, any of the known modifications of a radioimmunoassay can be used.

The tests are carried out in an analogous manner to the enzyme immunoassays described above using a radioactive label, e.g. $^{125}I$, instead of an enzyme label. The amount of immune complex formed which corresponds to the amount of polypeptides or derivatives thereof according to the invention or of Hodgkin lymphoma markers present in the test solutions is determined by measuring the radioactivity of the immune complex.

The antibodies according to the invention can be used as such or in the form of derivatives conjugated with chemiluminescent markers in a chemiluminescence immunoassay. The tests are carried out in an analogous manner to the enzyme immunoassays described above using a chemiluminescent label instead of an enzyme label. The amount of immune complex formed which corresponds to the amount of polypeptides or derivatives thereof according to the invention or of Hodgkin lymphoma markers present in the test solutions is determined by adding a compound triggering luminescence, e.g. $H_2O_2$ and NaOH, and measuring the emission of light with optical measuring devices.

For immnunostaining cryosections of cryopreserved biopsy material or paraffin embedded tissue sections are treated with a solution containing an antibody of the invention, then washed and developed with a second antibody binding to the antibody of the invention, which second antibody can be detected due to a radioactive label, an enzyme conjugated to it, a fluorescence marker, or biotin. Otherwise, the cryosection or embedded tissue is reacted with a solution of an antibody derivative of the invention as described hereinbefore, e.g. a radiolabelled derivative bearing $^{125}I$, a conjugate with an enzyme, e.g. with horseradish peroxidase, alkaline phosphatase or β-D-galactosidase, a conjugate with a fluorescent marker, e.g. with fluorescein, or a conjugate with biotin. Bound radiolabelled antibodies are detected by scanning the radioactivity of the tissue sections. Bound antibody conjugates with enzymes are detected after treatment with a suitable enzyme substrate, preferably an enzyme substrate which leads to a solid deposit (stain) at the site of the antibody or at the site of the second antibody binding to the antibody of the invention. In place of antibody conjugates with enzymes, antibody conjugates with biotin and a solution of avidin-enzyme-conjugate may be used, which leads to higher enzyme concentration at the site of the antibody and hence increased sensitivity of the immunostaining method. The solid deposit of the enzyme substrate is detected by inspection with a microscope or by scanning optical density at the wavelength of the stain. Staining by antibody conjugates with fluorescent markers is detected likewise.

The use according to the invention of antibodies and derivatives thereof as described hereinbefore for the determination of polypeptides or derivatives therof according to the invention or of Hodgkin lymphoma markers also includes other immunoassays known per se, for example immunofluorescence assays, latex agglutination with antibody-coated or antigen coated latex particles, hemagglutination with antibody-coated or antigen-coated red blood corpuscles, evanescent light assays using an antibody-coated optical fibre and other direct-acting immunosensors which convert the binding event into an electrical or optical signal, or the like.

The invention relates also to test kits for the qualitative and quantitative determination of polypeptides or derivatives thereof according to the invention or of Hodgkin lymphoma markers comprising polyclonal and/or monoclonal antibodies of the invention and/or derivatives thereof and, optionally, other polyclonal or monoclonal antibodies and/or adjuncts.

Test kits according to the invention for an enzyme immunoassay or enzyme immunostaining contain, for example, a suitable carrier, optionally freeze-dried solutions of one or more polyclonal and/or monoclonal antibodies, optionally freeze-dried or concentrated solutions of an enzyme- or biotin-conjugated antibody, solutions of an enzyme-avidin conjugate if biotin-labelled antibody is used, enzyme substrate in solid or dissolved form, standard solutions of a polypeptide of the invention or a derivative thereof, buffer solutions, and, optionally, polypeptides or detergents for preventing non-specific adsorption and aggregate formation, pipettes, reaction vessels, calibration curves, instruction manuals and the like. One or more of the antibodies of the test kit are antibodies of the invention.

Test kits according to the invention for a radioimmunoassay or a corresponding immunostaining test contain, for example, a suitable carrier, optionally freeze-dried solutions of one or more polyclonal and/or monoclonal antibodies, solutions of a radioactively labelled antibody, standard solutions of a polypeptide of the invention or a derivative thereof, buffer solutions, and, optionally, polypeptides or detergents for preventing non-specific adsorption and aggregate formation, pipettes, reaction vessels, calibration curves, instruction manuals and the like. One or more of the antibodies of the test kit are antibodies of the invention.

The antibodies and antibody derivatives of the invention can be used for the qualitative and quantitative determination of polypeptides of the invention or derivatives thereof. Due to the fact that these polypeptides or derivatives are mediators or precursors for mediators of inflammation, the antibodies and antibody derivatives of the invention are thus useful for the simple and reliable diagnosis of inflammatory conditions, in particular of delayed type hypersensitivity reactions. The presence or the amount of the polypeptides of the invention or their derivatives can be determined in biological fluids such as human serum, joint fluid or plasma, in tissue sections and cells by standard diagnostic procedures, for example immunoassays as described above, preferentially enzyme immunoassays.

The determination of polypeptides and derivatives thereof according to the invention can also be used to monitor the treatment of inflammatory conditions during therapy since measuring the level of the polypeptides and derivatives thereof can assess effectiveness of therapy.

Furthermore, the antibodies and antibody derivatives of the invention are useful as antagonists to the natural mediator and can therefore be used to control inflammatory processes. The antibodies and antibody derivatives of the invention can be used for the isolation and purification of the polypeptides or derivatives of the invention from natural sources or from transformed host cells by immunoaffinity chromatography.

In addition the antibodies and antibody derivatives of the invention can be used for the localization of Hodgkin lymphoma in a patient using radioscanning techniques. To that end, radiolabelled derivatives of antibodies binding to MRP-160, rMRP-70 or MRP-160 fragments are injected into the patient, and the patient scanned with a gamma imager at regular intervals. Cells expressing Hodgkin lymphoma markers will take up more radioactive antibodies than other tissue and will be clearly recognized by the gamma imaging camera. Preferentially monoclonal antibodies labelled with $^{131}I$ or with $^{99m}Tc$ are used for radioscanning in amounts of 3 to 8 µg representing 15 to 30 µCi per kg body weight.

Further, the antibodies themselves and particularly derivatives thereof such as conjugates with cytotoxic and carcinostatic compounds can be used for the treatment of Hodgkin lymphoma. The therapeutic dose for mammals is between approximatively 10 µg and 1 mg per kg body weight for antibodies themselves, and between 1 µg and 100 µg per kg body weight for conjugates with cytotoxic drugs, depending on the status of the patient and the mode of application.

The invention concerns also pharmaceutical compositions containing antibodies binding to MRP-160, rMRP-70 or MRP-160 fragments, or derivatives thereof, in a therapeutically effective amount together with a pharmaceutical carrier, solid or liquid, of organic or inorganic, for the treatment of Hodgkin lymphoma. Suitable pharmaceutical compositions are those described above, but containing antibodies of the invention in place of the polypeptide or polypeptide derivatives.

| Abbreviations | |
|---|---|
| BSA | bovine serum albumin |
| BCIP | 5-bromo-4-chloro-3-indolyl phosphate |
| CIAP | calf intestinal alkaline phosphatase |
| dNTP | deoxyribonucleoside triphosphate (N = adenine, cytosine, guanine or thymine) |
| DTT | dithiothreitol |
| FPLC | fast protein liquid chromatography |
| IPTG | isopropyl-β-D-thiogalactoside |
| L-broth | Luria broth |
| MAb | monoclonal antibody |
| NBT | nitro blue tetrazolium |
| OD | optical density |
| pdN6 | pNpNpNpNpNpN (N = deoxynucleotide), random 6-mer |
| rATP | (ribo)adenosine 5'-triphosphate |
| RT | room temperature |
| SDS | sodium dodecyl sulfate |
| TE buffer | Tris-EDTA buffer |
| U | unit(s) |

EXAMPLES

Example 1

Construction of the Human cDNA Libraries L132 and MNC 1.1 Isolation of mRNA from human L132 cells 1.1.1 Isolation of total RNA A 5 ml pellet of $8 \times 10^8$ L132 cells (ATTC CCL5, human embryonic epithelial lung cells) is dissolved in 20 ml of 0.8 µm filtered GuSCN solution containing 4M guanidine isothiocyanate, 25 mM sodium acetate pH 6 and 120 mM β-mercaptoethanol. After vigorous shaking, the DNA is partially sheared by ten successive passages through a 22G needle. The solution is layered on top of three CsCl-cushions consisting of 4 ml of a solution of 5.7M CsCl in 25 mM sodium acetate pH 6 in polypropylene tubes and is centrifuged for 16 hrs at 20° C. at 29,000 rpm in a TST41 rotor (Kontron). The supernatant is carefully removed, and the pellets are redissolved in 1.5 ml 0.2% SDS and extracted with 1.5 ml chloroform. The RNA is precipitated from the aqueous phase by addition of two volumes of ethanol, redissolved in 1.5 ml 0.2% SDS and reprecipitated by addition of sodium acetate pH 6 to 0.15M and two volumes of ethanol.

1.1.2 Isolation of mRNA

The RNA pellet containing 14 mg of total RNA is dissolved in 5 ml of elution buffer (10 mM Tris-HCl pH 7.5, 1 mM EDTA and 0.2% SDS), heated at 65° C. for 2 min and cooled quickly to room temperature. After addition o f 0.55 ml of 5M NaCl, the solution is applied three times to a column of 0.5 g of oligo-dT cellulose (type 7, Pharmacia) equilibrated in wash buffer (0.5M NaCl, 10 mM Tris-HCl pH 7.5, 1 mM EDTA and 0.2% SDS). After washing the column with 15 ml of wash buffer, the bound RNA is eluted in 4 ml of elution buffer. The eluted material is heated at 65° C. for 2 min, cooled, adjusted to 0.5M NaCl and re-applied to the re-equilibrated column (three times). After washing with 15 ml of wash buffer, the mRNA is eluted from the column in 4 ml of elution buffer and precipitated overnight at −20° C. after addition of 0.25 ml 3M sodium acetate pH 6 and 10 ml of ethanol. The precipitate (275 µg) is collected by centrifugation (15 min at 16,000 g), dissolved in 0.4 ml of H$_2$O and precipitated by addition of 25 µl sodium acetate (3M, pH 6) and 1 ml of ethanol. After chilling in dry ice for 10 min, the RNA is collected by centrifugation for 5 min in an Eppendorf centrifuge. The pellet is air dried and redissolved in 275 µl H$_2$O.

1.2 Synthesis of double stranded cDNA for cloning in bacteriophage lambda gt11

In the beginning, single-stranded cDNA is synthesized using the L132 mRNA of Example 1.1.2 or RNA from human peripheral blood mononuclear leukocytes (MNC; prepared as described in European Patent Application 0 263 072) as templates. Two 10 µg samples of L132 mRNA or 20 µg of MNC RNA are incubated for 1 hr at 43° C. each in 50 µl solution containing 100 mM Tris-HCl (pH 8.3, measured at 43° C.), 10 mM MgCl$_2$, 140 mM KCl, 10 mM DTT, 1 mM of each dNTP, 100 µg/ml of oligo-dT(12–18) (Pharmacia), 90 U of RNasin™ (Promega Biotech), 40 U of AMV reverse transcriptase (Genofit) and 5 µCi of α-$^{32}$P-dCTP (3000 Ci/mmol). After combining the two corresponding samples, the RNA-DNA hybrid molecules are recovered as follows: The sample is adjusted to a molarity of 20 mM in EDTA (pH 7.5) and 0.2% in SDS, extracted with an equal volume of phenol-chloroform (1:1, equilibrated with TNE: 100 mM NaCl, 10 mM Tris-HCl pH 8.0, 1 mM EDTA) and loaded on a 1.5 ml column of Sepharose-4B (Pharmacia, equilibrated in TNE containing 300 mM NaCl [total]). Upon washing the column with the same buffer, the fractions containing at least 90% of the material (judged by the incorporated $^{32}$P) are combined (4–5×50 µl), and two volumes of ethanol are added. After chilling in dry ice for 10 min, the precipitate is recovered by centrifugation for 5 min in an Eppendorf centrifuge, washed with 0.1 ml of 70% ethanol, and air-dried. The RNA-DNA hybrids are re-incubated for 1 hr at 43° C. in a 50 µl reaction as described above, with omission of the oligo-dT. The reaction mixture is then adjusted to 20 mM in EDTA, and 3.8 µl of 1N NaOH are added. The reaction mixture is then incubated for 20 min at 75° C., cooled, neutralized by addition of 25 µl of 1M Tris-HCl pH 8 and 6 µl of 1N HCl, and the single stranded cDNA is recovered as described above for the RNA-DNA hybrids.

For second strand synthesis, 5 µg of single-stranded cDNA are incubated for 30 min at 37° C. in 100 µl buffer containing 33 mM Tris-acetate pH 7.9, 66 mM potassium acetate, 10 mM magnesium acetate, 0.5 mM DTT, 1 mg/ml BSA (Pentax fraction V, Calbiochem), 10 ng/ml pdN6 (Pharmacia), 1 mM of each dNTP, 10 µCi of α-$^{32}$P-dCTP (3000 Ci/mmol) and 500 U/ml T4 DNA polymerase (FPLC-pure, Pharmacia). The double-stranded cDNA is recovered as described above for RNA-DNA hybrids.

In the next step, the cDNA is digested with S1 nuclease by the procedure described in the following. 6 µg of cDNA is incubated for 5 min at 37° C. in 50 µg of a solution containing 200 mM NaCl, 50 mM sodium acetate pH 4.5, 1 mM ZnSO$_4$ and 0.5% glycerol. 2.5 U of S1 nuclease (Pharmacia) are added, and the incubation is continued for 10 min. The DNA is recovered as described above for RNA-DNA hybrids.

Then, EcoRI methylation is carried out as follows. 4 µg of double-stranded cDNA are incubated for 20 min at 37° C. in 50 µl solution containing 100 mM Tris-HCl pH 8, 5 mM EDTA, 0.4 mg/ml BSA (Pentax fraction V, Calbiochem), 15 µM S-adenosyl methionine (Biolabs) and 100 U EcoRI methylase (Promega Biotech). The reaction is stopped by incubation at 65° C. for 10 min. After addition of 4 µl 0.5M EDTA, 100 µl TNE and 1 µl 20% SDS, the solution is extracted with phenol-chloroform and the DNA is recovered by ethanol precipitation as described above.

For treatment with T4 polymerase (Boehringer), 3 µg of cDNA are incubated for 15 min at 37° C. in 50 µl of a solution as described above for the second strand synthesis without pdN6, and DNA is recovered as described above for RNA-DNA hybrids.

Then, synthetic oligonucleotide linkers are ligated to the blunt ends of the DNA fragments with T4 ligase as described in the following. 2.5 µg of cDNA are incubated overnight at 15° C. in 30 µl solution containing 20 mM Tris-HCl pH 7.8, 10 mM MgCl$_2$, 1 mM DTT, 1 mM rATP, 3 A$_{260}$ U/ml EcoRI linker (pCCGGAATTCCGG, Biolabs) and 800 U of T4 ligase (Biolabs). The reaction is stopped by incubation at 65° C. for 10 min. After addition of 60 µl H$_2$O, 10 µl of a solution containing 1M NaCl, 0.5M Tris-HCl pH 7.5, 0.1M MgCl$_2$, 10 mM DTT and 90 U of EcoRI (Boehringer) are added and the reaction mixture is incubated at 37° C. for 3 hrs. The cDNA is recovered as described for RNA-DNA hybrids with the exception that after the ethanol precipitation the DNA is rechromatographed on a second Sepharose 4B column.

1.3 Cloning of cDNA in lambda gt11

25 ng of each of the cDNAs L132 and MNC of Example 1.2 are ligated overnight at 15° C. to 0.5 µg of dephosphorylated EcoRI-digested lambda gt11 arms (Promega Biotech) in 10 µl solution containing 20 mM Tris-HCl pH 7.8, 10 mM MgCl$_2$, 1 mM DTT, 1 mM rATP and 400 U T4 ligase (Biolabs).

The ligated DNAs are packaged by using Gigapack Gold™ packaging extracts (Stratagene) and incubation at 20° C. for 2 hrs as described by the manufacturer. 0.5 ml of SM buffer (phage dilution buffer consisting of 100 mM NaCl, 50 mM Tris-HCl pH 7.5, 8 mM MgSO$_4$, 0.01% gelatin) and 20 µl of chloroform are added and the phage suspension is stored at 4° C.

For the preparation of competent cells which can be transformed with lambda gt 11, 2 ml of an overnight culture of E. coli Y1090 (Promega Biotech) are added to 200 ml of TY medium (8g/l tryptone, 5g/l yeast extract, 2.5 g/l NaCl) supplemented with 0.2% maltose and 50 µg/ml ampicillin and incubated at 37° C. When the OD$_{600}$ reaches 0.7, the cells are collected by centrifugation and resuspended in 50 ml 50 mM MgSO$_4$.

10 µl of serial dilutions of the phage suspension described above are added to 100 µl of a suspension of competent Y1090 cells, incubated at 37° C. for 30 min, added to 4 ml of melted top-agar (55° C.) containing 20 µl of 20 mg/ml IPTG in H$_2$O and 20 µl of 20 mg/ml Blu-gal™ (BRL) in N,N-dimethylformamide, and plated on TY plates. After overnight incubation at 37° C., the titer for the phage suspension containing L132 cDNA is calculated to be 10$^7$/ml, 4% of which is wild type phage. The titer for the phage suspension containing mononuclear leukocyte cDNA is calculated to be 2×10$^6$, 30% of which is wild type.

Example 2

Screening of Lambda gt11 Murine and Human cDNA Expression Libraries for cDNA Encoding the Molecule Which Reacts With the Monoclonal Antibody 1C5

A cDNA library from linoleic acid induced mouse peritoneal macrophages (ML 1005B) and a cDNA library of uninduced human U937 cells (HL1029B), which are both lambda gt11 expression libraries and are purchased from Genofit, are screened using an immunoperoxidase technique. The screening is carried out to identify cDNA encoding the molecule that binds the monoclonal antibody 1C5 (MAb 1C5). This monoclonal antibody is described in the European Patent Appplication 0 162 812. It is produced by the murine hybridoma cell line with the designation 1C5 (CNCM deposition number I-316) and is specific for a human macrophage migration inhibition factor (MIF).

The cDNA libraries are titered to yield $2 \times 10^9$ phages per ml, diluted 1:1000 with SM buffer, and for each library ten aliquots (20 µl) are incubated for 20 min at RT with ten aliquots (1 ml) of a suspension of competent Y1090 cells of Example 1.3. 10 ml of melted TY top agar (60° C.) are added to each sample, which is plated on 15 cm TY agar plates. After 10 min, the plates are incubated at 42° C. for 3.5 hrs.

At RT a 0.45 µm nitrocellulose membrane (Schleicher and Schuell) is placed onto each plate, allowed to wet and sprayed three times with a film of 1.35 g/l IPTG in $H_2O$. After 10 min, the plates are incubated for 3.5 hrs at 37° C. After position-marking, the filters are rinsed in TBST buffer (150 mM NaCl, 10 mM Tris-HCl pH 8 and 0.05% Tween® 20), followed by slow rocking for 30 min at RT in the same buffer supplemented with 1% non-fat milk powder, and another rinse with TBST buffer.

The 2×10 filters are slowly rocked overnight at RT in 2×200 ml TBST buffer supplemented with 1% non-fat milk powder and 20 mg/ml of MAb 1C5. The filters are washed three times for 15 min with TBST and incubated for 30 min at RT with 2×200 ml alkaline phosphatase-conjugated goat anti-mouse IgG (Dianova), which is diluted 1:2500 with TBST supplemented with 1% non-fat milk powder. The filters are washed three times for 15 min with TBST.

The filters are developed by the addition of a color reagent which has the following composition: 100 mM Tris-HCl pH 9.5, 100 mM NaCl, 5 MM $MgCl_2$, 0.5% of a 75 mg/ml solution of NBT (Biorad) in 70% dimethylformamide and 0.33% of a 50 mg/ml solution of BCIP (Biorad) in 100% dimethylformamide. 10 ml color reagent is added per filter and the reaction is allowed to proceed at RT until signals have clearly appeared (up to 4 hrs), after which the reaction is stopped by placing the filters in a solution containing 20 mM Tris-HCl pH 8 and 5 mM EDTA.

Positive plaques are picked and shaken for 1 hr at RT in 1 ml SM buffer containing 20 µl chloroform. Serial dilutions in SM are plated and screened with MAb 1C5 as described above. The process is repeated until all plaques give a positive reaction. From each of the cDNA libraries, two positive plaques are isolated: M9 and M10 from the mouse library ML1005B, and H31 and H35 from the human library HL1029B.

Example 3

Isolation of cDNA Inserts of Recombinant Phase DNA M9, M10, H31 and H35

3.1 Isolation of recombinant phage DNA

100 µl of the phage suspensions of Example 2 and a suspension of competent Y1090 cells of Example 1.3 are mixed, left at RT for 20 min and added to 100 ml TY medium supplemented with 10 mM $MgSO_4$. After shaking at 250 rpm overnight in a 1 l flask at 37° C., 1 ml of chloroform and 100 µg of RNase A are added. After 30 min at RT, NaCl is added to give a molarity of 1M, and after 1 hr on ice the solution is cleared by centrifugation (20 min at 2,000 rpm in a H6000 Sorvall rotor). Polyethylene glycol 6000 is added to the supernatant to result in a final concentration of 10%, the mixture is left on ice for 1 hr, and the phage is pelleted by centrifugation (20 min at 3,000 rpm in a H6000 Sorvall rotor). The phage pellet is resuspended in 2 ml SM buffer supplemented with 100 µg RNase A and 50 µg DNase I. After 30 min at RT, the solution is extracted with 4 ml of chloroform followed by centrifugation (5 min at 1,500 g). The aqueous phase is adjusted to 10 mM EDTA, 0.1% SDS and 200 µg pronase, left at RT for 15 min and extracted with 4 ml of chloroform followed by centrifugation (5 min at 1,500 g). The aqueous phase is adjusted to 0.5M $NaClO_4$ and 33% 2-propanol. After 1 hr on ice the DNA is recovered by centrifugation (10 min at 10,000 g). The DNA is dissolved in 200 µl TE (10 mM Tris-HCl pH 8.0, 1 mM EDTA) and reprecipitated by addition of 200 µl 5M ammonium acetate and 0.8 ml 2-propanol followed by centrifugation (10 min at 10,000 g). After washing with 70% ethanol, the DNA is dissolved in 200 µl TE.

3.2 Isolation of cDNA inserts

10 µg of phage DNA are digested for 1 hr at 37° C. in 100 µl solution containing 100 mM NaCl, 50 mM Tris-HCl, 10 mM $MgCl_2$, 1 mM DOT and 50 U of EcoRI. The cDNA inserts are isolated by preparative agarose gel electrophoresis followed by electroelution. The sizes of the recombinant phage DNA inserts M9, M10, H31 and H35 of Example 2 all appear to be 2.3 kb.

3.3 Subcloning of the isolated cDNA inserts

The EcoRI cDNA inserts are subcloned into the vector pBLUKSP™ (Stratagene) using established procedures (T. Maniatis et al., "Molecular cloning, a laboratory manual", Cold Spring Harbor Laboratory, 1982).

Example 4

Identification of the Desired cDNA Sequences in the Human Lambda gt11 cDNA Libraries L132 and MNC by Cross-Hybridization The cDNA encoding the molecule which reacts with MAb 1C5 is identified in the human lambda gt11 cDNA libraries L132 and MNC of Example 1.3 by successive screening using MAb 1C5, the cDNA inserts of Example 3.2 and subfragments thereof.

$5 \times 10^5$ plaques each of the cDNA libraries L132 and MNC (constructed as descred in Example 1.3), of the commercially available cDNA libraries ML1005B and HL1029B (Example 2) and the uninduced human leukemia derived HL 60 library HL1020B (Genofit) are plated on ten 15 cm plates as described above in Example 1.3 with omission of IPTG and Blu-gal™. Two replica filters (NEF-978A, NEN) are made of each plate according to established procedures (T. Maniatis et al., "Molecular cloning, a laboratory manual", Cold Spring Harbor Laboratory, 1982). Several rounds of hybridization as described in the following are performed with the radioactively labelled probes listed in Table 1 below.

The hybridization procedure is carried out as follows. The filters are prehybridized for 2 hrs at 65° C. in a solution (10 ml/filter containing 2×Denhardt's solution, 6×SSC (saline-sodium citrate buffer, see T. Maniatis et al., loc. cit.), 0.2% SDS and 50 µg/ml of denatured calf thymus DNA. Hybridization is performed overnight at 65° C. in the same solution containing the heat denatured oligo-labelled cDNA probe ($3-6 \times 10^6$ dpm per filter) according to Table 1 below. Oligo labeling of the appropriate cDNA fragments is performed as follows: 0.1 µg of DNA in 13 µl is placed at 95° C. for 5 min, cooled and briefly centrifuged. After addition of 2 µl of 10×NT buffer (0.5M Tris-HCl pH 7.2, 0.1M $MgSO_4$, 1 mM DTT and 0.5 mg/ml BSA [Pentax fraction V, Calbiochem]), 1 μl of a solution containing 20 mM of each dGTP, dTTP and dATP, 3 μl of α-$^{32}$P-dCTP (10 mCi/ml, 3000 Ci/mmol), 1 μl pdN6 (1 mg/ml, Pharmacia) and 1 μl DNA polymerase I (5 U/μl, Boehringer), the mixture is incubated at 37° C. for 30 min. The labelled DNA (5×10$^8$ dpm/μg) is recovered as described for RNA-DNA hybrids in Example 1.2. After the hybridization, the filters are washed for 15 min at 65° C. in two changes of the following solutions: 2×SSC, 0.2% SDS; 1×SSC, 0.2% SDS and 0.5×SSC, 0.2% SDS. Positive plaques are visualized by autoradiography.

The cDNA subfragments identified in the individual libraries in the hybridization experiments are listed in Table 1 below. Of each probe cDNA fragment the name of the clone is given as well as the relative approximate location on the sequence of MRP-160 (see Example 5.2).

TABLE 1 cDNA clones used for hybridization

| probe used for identification of cDNA subfragments/location | designation of cDNA subfragments identified in each cDNA library | | | | |
|---|---|---|---|---|---|
| | ML1005B | HL1020B | HL1029B | L132 | MNC |
| 1C5 | M9, M10 | | H31, H35 | | |
| M10 insert 3500–5800 | M10.1 | H25 | (H35)* | | |
| M10.1 small EcoRI fragment 3020–3500 | | H23 | H12 | | |
| H23 HindIII-EcoRI fragment 3750–4710 | | H70 | H67, H69 | | |
| H23 PstI-EcoRI fragment 2735–3275 | | H4, H5 | | | |
| H4 EcoRI-KpnI fragment 140–1170 | | | | L4, L7 | |
| pMRP-160 BglII fragment 1-1160 | | | | | N2, N3 |
| pMRP-160 BglII fragment 3670–4720 | | | | | N1, N10 |

*pure phage plated

Example 5

Isolation and Determination of Nucleotide Sequences of the Overlapping cDNA Subfragments 5.1 Plaque purification Positive plaques identified by plaque hybridization as described in Example 4 are picked and serial dilutions are plated as described above in Examples 1.3 and 2. The purification cycle is repeated until all plaques are positive. Phage DNA is prepared and the cDNA inserts (see Table 1) are isolated and subcloned as described above in Example 3.

5.2 Sequence determination

Restriction enzyme analysis of the cDNA subfragments is performed using standard procedures. Convenient restriction fragments from the cDNA subfragments are cloned in the vectors PBLUSCRIPT™ or pUCK0 (K. Odink et al., Nature 330, 80, 1987).

cDNA sequence determination is carried out by the dideoxy nucleotide chain termination reaction method using double-stranded DNA and the sequenase™-kit and -protocol (United States Biochemical; M. Haltiner et al., Nucl.Acids Res. 13, 1015, 1985). Universal primers are obtained from Stratagene. For internal priming and sequence verification, primers as listed in Table 2 are synthesized (Y. Ike et al., Nucl.Acid Research 11, 477, 1983). The sequence is determined in both directions, and if restriction sites are used in the sequence strategy they are confirmed using the overlapping fragments and internal primers of Table 2.

TABLE 2

Oligonucleotide primers used for sequencing

| | | |
|---|---|---|
| 1. | H 0263s | ACTCCATCATCTGAGAC |
| 2. | H 0310r | ACTCGAAAGTCATCCAC |
| 3. | H 0600r | ATGCTGGCCGTAGAAGT |
| 4. | H 0621s | CCTTCAAACATCCCTCA |
| 5. | B 0793S | TGGTGGCACTAAGGCTG |
| 6. | B 0865r | CACGCCACACCACTCCC |
| 7. | H 0883s | GAAGAATGATGGCGCTG |
| 8. | H 0900r | CAGCGCCATCATTCTTC |
| 9. | B 1190s | TCCAGGAGGCCCTGAAG |
| 10. | H 1450r | AGGTCCTCAACCTTCCT |
| 11. | H 1601S | GGTGGCTACAGTTTCAG |
| 12. | H 1650r | GGTCTTTCTCCAGTTCC |
| 13. | B 1782r | GCTTCTAGCTTTTCTTG |
| 14. | B 1855s | GAAGGAGATAAAGGCTC |
| 15. | H 2053s | GAGACGGCAGAATTTGC |
| 16. | H 2379s | ACATCACAGCTCAAGGC |
| 17. | H 2513r | TTTAATCTGTTTCTCAG |
| 18. | H 2610s | AGTGAAAGAGACTTTGG |
| 19. | H 2884s | ATGTCAGGAGATAACTC |
| 20. | H 3111s | GAAATTGTCGGACCTGG |
| 21. | H 3157s | GCCAGGTATGAGAGAGC |
| 22. | H 3476s | ATGTGGAAGAGCTGAAC |
| 23. | H 3492r | GTTCAGCTCTTCCACAT |
| 24. | B 3605r | ACTTCTGAGCTGCTGCC |
| 25. | H 3731s | CCAAGTTCATAAAAGAC |
| 26. | H 4111r | CCACCTTCATCTTGAGG |
| 27. | H 4200s | CAGTCCAAGAAGAAACC |
| 28. | H 4250r | TCTGTGTCGTGGAGATC |
| 29. | H 4400s | CCTCCAGTGGAGAACTG |
| 30. | pUCK0r | CAGTGAGCGAGGAAGCG |

The number indicates the approximate location on the sequence of MRP-160 (see SEQ ID NO: 1). An H means that the oligonucleotide is predicted on the human sequence, a B means that the oligonucleotide will prime on both human and mouse sequences. Some oligonucleotides do not fit the MRP-160 sequence completely. Number 30 is a universal primer for pUCK0.

The 6 kb cDNA codes for a precursor protein of approximately 160 kD designated MRP-160. The full sequence of MRP-160 cDNA and the predicted amino acid sequence are shown in SEQ ID NO: 1. A sequence of 105 nucleotides, probably representing one exon, is found to be missing from clones H5 and N2. The position of the cDNA subfragments of Example 4 on the MRP-160 sequence are given in Table 3.

TABLE 3

Position of the overlapping cDNA subfragments

| cDNA subfragment | position on MRP-160 |
|---|---|
| H4 | 140–3330 |
| H5 | 1280–3680 |
| H23 | 2740–4720 |
| H70 | 3580–5830 |
| L4 | 1-* |
| L5 | 1-* |
| L7 | 400–3640 |
| N3 | 1–2000** |
| N2 | 7–3050 |
| N10 | 2229–5822 |
| N1 | 4065–5852 |

*aberrant 3'-ends; full sequence not known
**exact 3'-end not known

Example 6
Construction of pMRP160

A hybrid vector comprising the DNA coding for MRP-160 is constructed as described in the following.

5 μg of the vector pUCK0 are digested with EcoRI, dephosphorylated with CIAP and purified by agarose electrophoresis and electroelution (fragment a). 5 μg of the cDNA subfragment H23 are digested with EcoRI and PstI. The 1.4 kb fragment coding for the C-terminus of MRP-160 is purified by agarose gel electrophoresis and electroelution (fragment b). 5 μg of the cDNA subfragment L7 are digested with PstI and KpnI. The 2.1 kb fragment coding for the middle portion of MRP-160 is purified by agarose gel electrophoresis and electroelution (fragment c). 5 μg of the cDNA subfragment L4 are digested with EcoRI and KpnI and the 1.2 kb fragment coding for the N-terminal portion of MRP-160 is purified by agarose gel electrophoresis and electroelution (fragment d).

0.1 μg of fragments a and c and 0.05 μg of fragments b and d are ligated and transformed into competent DH5α cells (Gibco). Recombinant DNA is isolated and analyzed by restriction analysis. A plasmid yielding a 4.7 kb EcoRI fragment as well as 1.2 and 3.5 kb EcoRI-KpnI fragments and 0.5 and 2.7 kb PstI-EcoRI fragments is designated pMRP160.

The sequence of the MRP-160 coding region is confirmed by sequencing using oligonucleotide primers as described above.

Example 7

Construction of pMRP70$_{pL}$

A hybrid vector comprising the coding part of the DNA of the H-23 subfragment is constructed as described in the following.

Subclones of the H23 cDNA insert in PBLUKSP™ are analyzed by restriction analysis. A clone yielding a 1.2 kb XhoI fragment is designated pH23.

10 μg of pH23 are digested with HincII and repaired with Klenow polymerase. The 1.8 kb fragment containing the coding part of H23 as well as 33 nucleotides of linker is isolated by agarose gel electrophoresis and electroelution (fragment a). 10 μg of the vector pP$_L$mu-bio (obtained from Biogen, derived from pP$_L$muSMCori [G. Buell et al., Nucl. Acids Research 13, 1923, 1985] by replacement of the NcoI-HindII fragment with the pUC9 polylinker) are digested with NcoI. The sticky ends are filled with Klenow polymerase, and the DNA is dephosphorylated with CIAP. The 3 kb vector is isolated by agarose gel electrophoresis and electroelution (fragment b).

0.1 μg of fragments a and b are ligated and transformed into competent *E. coli* K12 lambda lysogen strain. Recombinant plasmids are isolated and analyzed by restriction digestion. A plasmid yielding a BamHI-XhoI fragment of 0.6 kb is designated pMRP70$_{PL}$. The correct construction of pMRP70$_{PL}$ is confirmed by sequencing.

pMRP70$_{PL}$ is retransformed in competent LC137 cells (SC936; G. Buell, loc. cit., and S. Goff et al., Proc.Natl.Acad.Sci.USA 81, 6647, 1984) containing the plasmid pCI857 carrying a temperature sensitive CI gene (E. Remaut et al., Gene 22, 103, 1983). Transformants are selected by kanamycin plus ampicillin resistance. Cells containing pMRP70$_{PL}$ are stored as glycerol culture at −70° C.

Example 8

Fermentation of rMRP-70

The peptide rMRP-70 which is encoded by pMRP70$_{PL}$ is expressed in *E. coli* as described in the following.

Cells harboring pMRP70$_{PL}$ are streaked from a glycerol culture on a kanamycin/ampicillin plate and incubated at 30° C. From a single colony, a 12 ml culture is grown for 6 hrs at 30° C. in LBMKA (L-broth containing 50 μg/ml ampicillin and 40 μg/ml kanamycin) (culture a). Ten 200 ml LBMKA in 2 l flasks are inoculated with 1 ml of culture a and shaken at 30° C. overnight. The cultures are diluted with 800 ml 30° C. LBM and allowed to grow for another 3 hrs (cultures b). Synthesis of rMRP-70 is induced by quickly heating the cultures b to 42° C. in a 50° C. waterbath, followed by shaking at 42° C. for 2 hrs (cultures c). Cells from cultures c are collected by centrifugation.

Example 9

Purification and Characterization of rMRP-70

9.1 Cell extraction

*E. coli* cells expressing rMRP-70 grown to an optical density of 1.2 OD/ml units from 10 liter fermentation broth of Example 8 are disrupted with 250 ml of 8M guanidinium hydrochloride, 50 mM Tris-HCl, 30 mM NaCl, pH 8.0, containing 6 ml of 100 mM phenylmethylsulfonyl fluoride (PSMF) in 2-propanol. The suspension is centrifuged for 60 min at 20,000 g at 4° C. The supernatant is made 0.1% in dithiotreitol (DTT) and dialyzed (Spectrapor membrane No.3; 3.5 kD cutoff; Spectrum Medical Industries) at 4° C. against 10 mM Tris-HCl, 0.01% DTT, pH 8.0. The white precipitate formed is removed by centrifugation for 30 min at 20,000 g at 4° C.

9.2 DEAE ion exchange chromatography

The supernatant of Example 9.1 is pumped on a DEAE-Trisacryl M (LKB) ion exchange column (5×10 cm) equilibrated with the dialysis buffer. After loading of the sample, the column is washed with dialysis buffer until the UV 254 nm absorption reaches baseline level. Proteins bound to the column are eluted using a linear gradient of NaCl in dialysis buffer ranging from 0.0M to 0.2M NaCl (600 ml), then dialysis buffer/0.2M NaCl (200 ml) and dialysis buffer/0.1M NaCl (200 ml) at a flow rate of 4 ml/min. Individual 12 ml fractions are collected and analyzed by SDS-PAGE (U.K. Laemmli, Nature 227, 680, 1970) on 15% polyacrylamide slab gels (staining with Coomassie Blue R-250) and pooled according to their rMRP-70 content. Fractions from 0.12 to 0.2M NaCl are pooled, dialyzed against dialysis buffer and rechromatographed using the same procedure with the exception of the column dimensions (2.6×10 cm), buffer volumes (50%) and flow rate (2 ml/min). Fractions from 0.16 to 0.2M NaCl are pooled and concentrated 10-fold by ultrafiltration in a stirred cell (YM-10 membrane, Amicon).

9.3 Size exclusion chromatography 2 ml of the concentrated pool after ultrafiltration of Example 9.2 (protein concentration 14 mg/ml) are separated on an UltroPac TSK-G 2000 SWG (LKB) (21.5×600 mm) column in 20 mM sodium phosphate, 150 mM NaCl, pH 7.0 at a flow rate of 3 ml/min.

UV absorption is monitored at 280 nm and individual 6 ml fractions are analyzed by SDS-PAGE as described in Example 9.2. Fractions taken between 32 and 36 min after injection of the sample are pooled and concentrated 7-fold by ultrafiltration in a stirred cell (YM-10 membrane, Amicon).

9.4 Ion exchange chromatography on FPLC-Mono Q™

4 ml of the concentrated pool after ultrafiltration of Example 9.3 (protein concentration 4.9 mg/ml) are loaded onto a Mono Q™ HR 10/10 column (10 mm×100 mm) (Pharmacia) equilibrated in 20 mM diethanolamine/HCl, pH 8.5 (starting buffer). The column is washed at a flow rate of 4 ml/min for 10 min with starting buffer. Proteins are then eluted by a linear gradient over 20 min ending with starting buffer/0.1M NaCl. The eluate is monitored for absorbance at 280 nm. rMRP-70 is eluted between 21 and 23 min after injection of the sample (ca. 0.55 to 0.65M NaCl).

9.5 Reversed phase HPLC

Alternatively to the purification by size exclusion HPLC described in Example 9.3 or FPLC on Mono Q described in Example 9.4, the concentrated pool after ultrafiltration of Example 9.2 is acidified with ¹⁄₁₀ of the volume of 10% trifluoroacetic acid (TFA) and purified on a Vydac 214TP510 HPLC column (10×250 mm) (The Separation Group, Hesperia, Calif., USA). The column is equilibrated in a mixture of 70% TFA 0.1% in water and 30% TFA 0.08% in acetonitrile, and the product is eluted by a linear gradient over 24 min ending with a mixture of 50% TFA 0.1% in water and 50% TFA 0.08% in acetonitrile at a flow rate of 1 ml/min. The eluate is monitored for absorbance at 220 nm and individual peaks are collected manually according to the UV absorbance. Two main peaks are obtained at 15 min and 16.5 min, respectively, and analyzed as described below in Example 9.6.

9.6 Analysis by SDS-PAGE

Aliquots of fractions from the reverse phase column of Example 9.5 are dried in vacuo, dissolved in dissociation buffer, heated for 2 min at 96° C. and applied to a 15% polyacrylamide gel (staining with Coomassie Blue R-250). The 15 min peak of Example 9.5 contains several shortened versions of rMRP-70 of approximate apparent molecular weights of 55 kD, 44 kD, 38 kD and 33 kD, respectively. The material of the 16.5 min peak consists of pure rMRP-70 migrating in a single band with an approximate molecular weight of 70 kD.

9.7 Amino acid sequence analysis

The purified rMRP-70 of Example 9.6 is subjected to N-terminal amino acid sequence analysis using a gas-phase sequencer (Model 470, Applied Biosystems) according to the method of M. W. Hunkapillar and L. E. Hood (Methods in Enzymol. 91, 399, 1983). The anilino-thiazolinone derivatives are rearranged to phenylthiohydantoin (PTH) amino acids by treatment with 25% aqueous TFA at 50° C. The PTH amino acids are analyzed on a Zorbax™ CN HPLC column (DuPont; 200×4.6 mm) according to R. Knecht et al. (Anal. Biochem. 130, 65, 1983). The following N-terminal amino acid sequence is found: Met-Asp-Gly-Ile-Asp-Lys-Leu-Asp-Ile-Glu-Phe-Gly-Asn-Met-Leu-Ser. The amino acid sequence exactly matches the sequence predicted from the cDNA construction described in Example 5.2.

9.8 Immunofluorescence analysis

Monocytes in Teflon bags are harvested after three days culture in Mc Coy's medium (Biochrom, Berlin, FRG) supplemented with 20% human serum by centrifugation for 10 min at 150 g, washed in PBS and incubated for 30 min at 4° C. in 1% BSA, 1 µg/ml mouse IgG in 1 ml PBS/1×10⁷ cells. The cells are washed twice in PBS and aliquoted to 1×10⁶ cells per testpoint in 1.5 ml Eppendorf vials. Incubation in a proper dilution of rMRP-70 or natural human MIF (European Patent Application 0 162 812) (100 µl/1×10⁶ cells in PBS) is performed for 10 min at 4° C. The cells are washed twice in PBS and incubated 45 min with either biotinylated monoclonal antibody 1C5 (mouse, see EP 0 162 812) or anti-rMRP-70 serum (rabbit). Controls are biotinylated mouse IgG or normal rabbit IgG, respectively. After two washes in PBS/0.05% BSA the cells are incubated with streptavidin-FITC (Sigma, Müinchen, FRG) for the biotinylated antibody-treated probes and with goat anti-rabbit F(ab')₂-FITC (Dianova, Hamburg, FRG) for the rabbit antiserum-treated probes for 45 min at 4° C. The cells are washed twice in PBS/0.05% BSA. Before the last wash the cells are resuspended in 100 µl 1 mM Propidiumjodide in PBS, incubated 5 min at 4° C., washed, and analyzed in an EPICS™ cell sorter (Coulter Electronics, Hialeah, Fla., USA). Red fluorescent cells are electronically excluded from the green fluorescence measurement of the cells. The percentage of green fluorescence positive cells is calculated with the immuno-program supplied by Coulter Electronics.

The relative amount of the fluorescent cells is similar for rMRP-70 and natural MIF. This indicates that both natural MIF and rMRP-70 bind to cultivated monocytes.

9.9 Migration inhibition test

Buffy coat monocytes cultivated for one day in Dulbecco's medium supplemented with 10% FCS (Biochrom, Berlin, FRG) on Teflon membranes are harvested by centrifugation for 10 min at 150 g, washed twice in Dulbeco's medium without FCS and aliquoted to 2×10⁶ cells/testpoint in 1.5 ml Eppendorf vials. The cells are resuspended and incubated for 10 min at 4° C. with 200 µl PBS with or without a proper dilution of rMRP-70 or natural MIF (EP 0 162 812). The cells are centrifuged 5 min at 150 g, washed, resuspended in 200 µl PBS and incubated for 30 min at 37° C.

After washing with PBS the pelleted cells are resuspended in 4 µl Dulbecco's medium containing 0.2% low melting agarose (Miles, Frankfurt, FRG) at 37° C. One µl of cell suspension is pipetted into one of the inner 60 wells of a 96 well plate. Each sample is tested in duplicate. The plate is kept at 4° C. for 10 min. The wells are filled with 100 µl/well Dulbecco's medium, 10% FCS and incubated for 16–24 hrs at 37° C. in moist air containing 7% CO₂.

After incubation the migration of monocytes out of the agarose droplets is measured with the aid of a graduated reticule in the ocular of a microscope. The migration of the cells in the control solution is set as 100% migration or 0% migration inhibition. The migration distance is expressed as per cent migration inhibition. A substance is considered biologically active when it causes more than 30% migration inhibition.

The results of the migration inhibition test with rMRP-70 are summarized in Table 4 below.

TABLE 4

Migration inhibition of cultivated monocytes by rMRP-70

| concentration of rMRP-70 µg/ml | migration inhibition |
|---|---|
| 0.001 | 15% |
| 0.01 | 24% |
| 0.1 | 50% |
| 1 | 57% |
| 10 | 43% |

Example 10

Construction of the Expression Vector pCDEX

10 µg of pSV0d DNA (P. Mellon et al., Cell 27, 279, 1981) are digested with HindIII. The sticky ends are filled with Klenow polymerase, and after heat inactivation of the polymerase the DNA is digested with NaeI. The 2.2 kb vector fragment carrying the SV40 origin of replication is isolated by agarose gel electrophoresis and electroelution (fragment a). 10 µg of pCGA28 DNA (European Patent Application 0 305 967) are digested with BamHI. The sticky ends are filled with Klenow polymerase, and the DNA is dephosphorylated with calf intestinal phosphatase. The 3.9 kb fragment carrying the murine cytomegalovirus (MCMV) promoter/ enhancer, tPA cDNA and a β-globin splice donor/acceptor and poly-addition site, is isolated by agarose gel electrophoresis and electroelution (fragment b). Approximately 50 ng of the fragments a and b are ligated and transformed into competent DH5α cells. Recombinant plasmids are isolated and analyzed by digestion with PvuI and HindIII. A plasmid yielding a 1.4 kb and a 4.8 kb fragment is designated pCON10.5 µg of pCON10 are digested with XmaI and dephosphorylated with CIAP (fragment d). The DNA is purified by agarose gel electrophoresis and electroelution.

1 µg of an adaptor (Biolabs #1101) with the sequence 5'-GATCCCCGGG-3' is kinased with T4 polynucleotide kinase and ligated with T4 ligase. After heat inactivation of the ligase, the DNA is digested with XmaI. After extraction with phenol/chloroform, the DNA is precipitated with ethanol (adaptor e).

50 ng of DNA fragment d is ligated to 50 ng of adaptor e and transfected into competent DH5α cells. Recombinant DNA is isolated and analyzed by digestion with BamHI and HindIII. A plasmid yielding fragments of 1.7 kb and 4.4 kb is designated pCDEX.

Example 11

Construction of pMRP160$_{ex}$

5 µg of pMRP160 are digested with EcoRI and the sticky ends are filled with Klenow polymerase. The 4.7 kb fragment coding for MRP-160 is isolated by agarose gel electrophoresis and electroelution (fragment a). 5 µg of pCDEX are digested with HindIII and BamHI. The sticky ends are filled with Klenow polymerase and the DNA is dephosphorylated with CIAP. The 4.5 kb vector fragment is isolated by agarose gel electrophoresis and electroelution (fragment b). 0.1 µg of the fragments a and b are ligated and transformed into competent DH5α cells. Recombinant DNA is isolated and analyzed by restriction analysis. A plasmid yielding a 0.6 kb KpnI fragment as well as an XhoI fragment of 4.1 kb is designated pMRP160$_{ex}$.

The sequence of the MRP-160 coding region is confirmed by sequencing using oligonucleotide primers as described above.

Example 12

Expression of pMRP160$_{ex}$ in Chinese Hamster Ovary Cells 12.1 Transfection of CHO cells with pMRP160$_{ex}$ and selection of transfected clones The plasmid pMRP160$_{ex}$ is expressed in Chinese hamster ovary (CHO) cells of line DUKXB 1, a mutant lacking the enzyme dihydrofolate reductase (G. Urlaub et al., Proc. Natl. Acad. Sci. USA 77, 4216, 1980). The cells are cultured in α-MEM (minimum essential medium) containing nucleosides and 5% fetal calf serum (all from Gibco). Cells are plated at a density of $10^4$/cm$^2$ in 6-well plates (3.4 cm$^2$ diameter, Nunc) and are cotransfected with 4 µg DNA of plasmid pSV2-neo (P. Southern and P. Berg 1, 327, 1982) following standard procedures as described in detail in U.S. Pat. No. 4,399,216, by R. J. Kaufman and P. A. Sharp (J. Mol. Biol. 159, 601, 1982) and by Asselbergs et al. (J. Mol. Biol. 189, 401, 1986). In a second experiment, 0.4 µg DNA of the plasmid pND2 (DHFR) is cotransfected with 0.4 µg DNA of pMRP160$_{ex}$ and 0.4 µg of pSV2-neo (Asselbergs et al., loc. cit.).

48 hrs later, the transfected cells are trypsinized and transferred to three Petri dishes (8.0 cm$^2$ in diameter, Nunc). The next day, the non-selective medium is replaced by selective medium (α-MEM without nucleosides containing 5% (v/v) dialyzed fetal calf serum and 1.0 mg/ml geneticin [Gibco]).

After two weeks, 18 geneticin resistant clones are isolated and examined for the expression of MRP-160 with a single cell assay using the affinity purified rabbit anti-rMRP-70 antibodies of Example 14.2 following established protocols (Suter et al., Cancer Immunol. Immunother. 16, 53, 1983). Four clones stain selectively with the anti-rMRP-70 IgG. They are designated 1B8, 2A2, 2B1 and 2B3. Of these clones, 2A2, 2B1 and 2B3 have been cotransfected with the plasmid pND2.

Immunoblotting (H. Towbin et al., Proc. Natl. Acad. Sci. USA 76, 4350, 1979) with cellular lysates of these transfectants indicates that under reducing conditions (U.K. Laemmli, Nature 227, 680, 1970), the rabbit anti-rMRP-70 antibodies react with molecular weight species of 120 and 140 kD.

12.2 Selection of clones expressing amplified MRP-160 sequences with methotrexate A subconfluent culture of CHO clone 2B1 is pretreated with 20 nM methotrexate (MTX, Sigma) for 24 hrs and then split 1:20 into Petri dishes of 8 cm diameter (Nunc). The cells are propagated in the selective medium α-MEM without nucleosides supplemented with 5% dialyzed fetal calf serum and 0.05 mg/ml gentamycin (all from Gibco) (R. Kaufman and P. A. Sharp, loc. cit.). The selection is initiated after 24 hrs by adding 20 nM MTX to the Petri dish. After 14 days, the resistant colonies are pooled and cloned by limiting dilution into 96-well plates (Falcon) in selection medium containing 50 nM MTX. Of 16 clones isolated, three are strongly positive with the rabbit anti-rMRP-70 antibodies. The clone designated 2B1-B4 is recloned by limiting dilution in selection medium containing 100 nM MTX. 8 resistant clones are selected, all of which react with rabbit anti-rMRP-70. The clones designated 2B1-B4C2 and 2B1-B4E3 are subjected to stepwise increments of MTX concentration up to 500 nM.

12.3 MRP-160 levels in cellular lysates and culture supernatants of the amplified CHO clones For the quantitative determination of rMRP-70 and MRP-160 in cellular lysates and culture supernatants of the amplified CHO clones 2B1-B4C2 and 2B1-B4E3, a two-site enzyme linked immunosorbent assay (ELISA) is performed.

12.3.1 Preparation of cellular lysates and culture supernatants

For production of culture supernatant, the CHO clones 2B1, 2B1-B4C2, 2B1-B4E3 and the CHO mock transfected clone 3AB (Example 12.1) are grown to subconfluency and incubated with α-MEM supplemented with 5% dialyzed fetal calf serum for 48–72 hrs. The clones 2B1-B4C2 and 2B1-B4E3 received in addition 200 nM MTX. After harvesting, the supernatants are centrifuged at 2,000 g for 15 min, then at 12,000 g for 15 min and stored at −80° C.

The preparation of cell lysates is performed following standard protocols. Briefly, the trypsinized cells ($2 \times 10^7$/ml) are treated with lysis buffer (100 mM Tris, 100 mM NaCl, 1 mM EDTA, 0.1% SDS [all Biorad], 1.0% Nonidet P40 [Shell], 1.0 mM phenylmethylsulfonyl fluoride [Boehringer Mannheim], pH 7.5; R. J. Kaufman and P. A. Sharp, loc.cit.) for 15 min on ice. After spinning down the cellular debris at 2,000 g for 15 min, the supernatant is centrifuged at 12,000 g for 15 min and stored at −80° C. The total protein concentration is determined according to the method of Lowry et al. (J. Biol. Chem. 193, 265, 1951).

12.3.2 Two-site ELISA

Aliquots of the cellular lysates and culture supernatants of the mock transfectant 3AB, of the parental transfectant 2B1 and of the MTX treated clones 2B1-B4C2 and 2B1-B4E3 are tested for their concentration of rMRP-70 and MRP-160 with the two-site enzyme linked immunosorbent assay (ELISA) described in the following. The ELISA is performed using the affinity purified rabbit anti-rMRP-70 antibodies of Example 14.2 following standard protocols (E. Engvall and P. Perlman, Immunochem. 8, 871, 1971; J. Brueggen et al., Cancer Immunol. Immunother. 15, 200, 1983). Rabbit anti-rMRP-70 IgG (1.0 µg/ml) in 0.05M carbonate buffer pH 9.6 is coated at 100 µl/well into 96-well plates (Nunc FI) and incubated overnight at 4° C. After blocking the nonspecific sites with Tris buffered saline (TBS, 0.05M, pH 7.4) containing 0.2% gelatin (Biorad), 1.0% bovine serum albumin (Serva) and 0.05% Tween® 20 (Biorad) for 1 hr at room temperature, the test samples (50 µl), recombinant rMRP-70 standards (1.9–250 ng/ml, see Example 9) and controls diluted in blocking buffer are added for 1 hr at 37° C. The plates are washed (Skatron Microwash II) with TBS containing biotinylated anti-rMRP-70 IgG (50 µl, 0.5 µg/ml; biotinylation according to a modified protocol of Lerner et al., J. Exp. Med. 152, 1085, 1980) for 30 min at 37° C. After washing, 50 µl of streptavidin alkaline phosphatase conjugate (Gibco BRL) is added for 30 min at 37° C. The bound enzyme is incubated with 100 µl of p-nitrophenyl phosphate (1.0 mg/ml in diethanolamine buffer 1M, pH 9.8; Sigma) for 30 min at ambient temperature, and then stopped with 0.5N HCl. The absorbances are read at 405 nm (Multiscan MCC, Flow). The data are reduced using a 4-parameter logistic curve fitting program (Flow).

The results of the ELISA are summarized in Table 5 below.

TABLE 5 rMRP-70 and MRP-160 levels in cellular lysates and supernatants of the transfected CHO cells[a]

| cell line | cell lysate[b] (ng MRP-70/mg protein) | culture supernatant[c] (ng MRP-70/ml/$10^6$ cells) |
|---|---|---|
| 2B1 (parental cell) | 23.0 | 0.0 |
| 2B1-B4C2 (MTX-treated) | 1250.0 | 56.0 |
| 2B1-B4E3 (MTX-treated) | 892.0 | 66.0 |
| 3AB (mock control) | 0.0 | 0.0 |

[a]two site ELISA; rabbit anti-rMRP-70 versus biotinylated rabbit anti-rMRP-70; values are in ng/ml, based on the recombinant rMRP-70 standard; the limit of detection is 1.0 ng/ml
[b]related on mg of total cellular protein
[c]supernatants are harvested after 72 hrs starting with subconfluent cell cultures The MTX treated clones express intracellulary approximately 50 times more of rMRP-70 related protein than the parental cell 2B1. The supermatants of the MTX clones contain 50–60 ng/ml/$10^6$ cells of immunoreactive protein, whereas the parental cell 2B1 is negative.

Example 13

Induction of Inflammatory Reaction in the Skin of Guinea Pigs

MRP-160 is tested for the ability to induce skin reactions in a test using normal guinea pigs.

Normal guinea pigs are shaved, anaesthesized and injected intradermally with 100 µl each of the supernatant of several MRP-160 amplified CHO cell lines. The skin reaction is determined after 24 hrs and 48 hrs. Positive reactions result in a significant reddening in an area of about 5–12 mm in diameter. Several MRP-160 amplified CHO cell lines are found to induce skin reactions whereas neither control cells cultured and injected under identical conditions nor the culture medium itself produced any effect.

Example 14

Preparation of Polyclonal Antibodies 14.1 Preparation of rabbit anti-rMRP-70 serum 0.5 mg rMRP-70 (prepared as described in Examples 8 and 9) in complete Freund's adjuvant (Gibco) are injected into rabbits followed by a booster injection of 0.5 mg rMRP-70 in incomplete Freund's adjuvant (Gibco) after 20 days. The titer of the rabbit serum is monitored by an enzyme-linked immunosorbent assay (ELISA) in microtiter plates coated with rMRP-70 following established protocols (E. Engvall and P. Perlman, Immunochem. 8, 871, 1971). Examination of Western blots reveals that, after exhaustive adsorption with lysates of untransfected *E. coli* cells, the only reactivity left in the serum is directed against rMRP-70.

14.2 Isolation of polyclonal rabbit antibodies specific for rMRP-70 by immunoaffinity chromatography An rMRP-70-Affigel 10 immunoadsorbent column is prepared by coupling of 4–5 mg of purified rMRP-70 to 1 ml of Affigel® 10 using the manufacturer's procedure (Bio-Rad). Immunoglobulin G (IgG) from the monospecific rabbit anti-rMRP-70 serum of Example 14.1 is precipitated by ammonium sulfate at 50% saturation. The precipitate is dissolved in PBS and dialysed against PBS. 15 ml of the dialysed solution containing approximately 100 mg of IgG is pumped through the immunoaffinity column at a flow rate of 10–12 ml/hr. Unspecifically bound material is removed by washing the column with PBS/0.4M sodium chloride. Specifically bound IgG is eluted with 0.1M glycine hydrochloride pH 2.5. Fractions containing the antibodies are pooled, neutralized by adding 1M Tris and dialysed against PBS. Approximately 4 mg of IgG specific for rMRP-70 are obtained.

14.3 Preparation of oligopeptides representing fragments of MRP-160

The following oligopeptides are synthesized by stepwise solid phase peptide synthesis with 9-fluorenylmethoxycarbonyl (Fmoc) protected amino acids as their preformed 1-hydroxybenzotriazole esters in N-methylpyrrolidone using the method described in H. Rink et al., Peptides: Chemistry, Structure and Biology (Ed. J. E. Rivier and G. R. Marshall), ESCOM, Leiden 1990, p. 1041.

MRP-160 fragment 1: Glu-Glu-Glu-Arg-Ser-Val-Leu-Asn-Asn-Gln-Leu-Leu-Glu-Met-Met-Lys-Lys corresponding to amino acids 1189-1204 of SEQ ID NO:1

MRP-160 fragment 2: Arg-Asn-Glu-Val-Thr-Val-Leu-Arg-Gly-Glu-Asn-Ala-Ser-Ala corresponding to amino acids 1242-1255 of SEQ ID NO:1

MRP-160 fragment 3: Glu-Ile-Cys-Glu-Met-Phe-Gly-His-Trp-Ala-Thr-Asn-Cys-Asn-Asp-Asp-Glu-Thr-Phe corresponding to amino acids 1409-1427 of SEQ ID NO:1

MRP-160 fragment 4: Ser-Thr-Pro-Ser-Asn-Ile-Pro-Gln-Lys-Pro-Ser-Gln-Pro-Ala-Ala-Lys corresponding to amino acids 162-177 of SEQ ID NO:1

14.4 Rabbit antisera directed against MRP-160 fragments 1, 2, 3 and 4

0.5 mg of each of the four oligopeptides of Example 14.3 in complete Freund's adjuvant (Gibco) are injected into four different rabbits followed by a booster injection in incomplete Freund's adjuvant (Gibco) after 20 days. The titer of the rabbit sera is monitored by an enzyme-linked immunosorbent assay (ELISA) in microtiter plates (Nunc) coated with the respective peptides as in Example 14.1. Immunoglobulin G (IgG) is precipitated from the sera with 50% ammonium sulfate.

An Affigel 10 immunoadsorbent column is prepared by coupling 4–5 mg of the respective MRP-160 fragment 1, 2, 3 and 4 to 1 ml of Affigel® 10 using the manufacturer's procedure (BioRad). The four precipitates of IgG are dissolved each in PBS and dialysed against PBS. 15 ml of the dialysed solutions of the respective anti-MRP-160 fragment IgG precipitates containing approximately 100 mg of IgG are pumped through the immunoaffinity column at a flow rate of 10–12 ml/hr. IgG is eluted as described in Example 14.2. Approximately 4 mg of IgG specific for the respective MRP-160 fragment 1, 2, 3 and 4 are obtained.

Example 15

Preparation of Hybridoma Cells Producing Monoclonal Antibodies Against rMRP-70

15.1 Immunization protocol

Three female Balb/c mice are injected each intraperitoneally with 0.1 mg of rMRP-70 in complete Freund's adjuvant (Gibco) followed by two booster injections of 0.05 mg rMRP-70 in incomplete Freund's adjuvant (Gibco) at 14 days interval. After 6 weeks, 0.05 mg of rMRP-70 in physiological saline are injected, and the mice are sacrificed 4 days later.

15.2 Cell fusion and selection of hybridomas

All fusions are performed following established protocols (G. Köhler and C. Milstein, Nature 256, 495, 1976) using the non-secreting myeloma cell line P3x63Ag8.653 (ATCC No. CRL 1580). $10^8$ spleen cells are fused with $10^7$ myeloma cells in the presence of 35% (w/v) polyethylene glycol (PEG 4000, Merck) and of 15% dimethyl sulfoxide (Merck). The fusion mixture is distributed in standard HAT selection medium supplemented with 20% FCS (Gibco) in 1200 wells of microtiter plates (Falcon) containing mouse peritoneal exudate cells as feeder cells. After 10–14 days, the supernatants of growing hybridomas are tested for binding of rMRP-70 with a sandwich ELISA (Example 16). Positive hybridomas are recloned by limiting dilution at least two times.

15.3 Expansion of hybridomas and isolation and purification of monoclonal antibodies specific for rMRP-70

Balb/c mice 8–10 weeks of age are pre-treated intraperitoneally (i.p.) with 0.3 ml pristane (Aldrich). 2–3 weeks later, 5–10×$10^6$ cloned hybridoma cells and 0.2 ml pristane are injected i.p. After 8–10 days ascites fluid is collected, centrifuged at 800 g and stored at –80° C.

Alternatively, the hybridomas are propagated in vitro at a large scale using hybridoma medium (Gibco). The supernatant is centrifuged at 800 g, filtered with a 0.45 µm Nalgene® filter and stored at –80° C.

Crude immunoglobulin is precipitated by dropwise addition of 0.9 volume equivalents of saturated ammonium sulfate at 0° C., then dissolved in 20 mM Tris-HCl, 50 mM NaCl, pH 7.9. An IgG fraction is obtained by using the Affigel® Protein A MAPS Kit procedure of Bio-Rad. The eluted IgG fraction is precipitated again with ammonium sulfate and dissolved in PBS at a concentration of 10 mg/ml and dialysed against the same buffer.

Example 16

Enzyme Immunoassay for Detection of MRP-160, rMRP-70 or MRP-160 Fragments 16.1 Biotinylation of polyclonal and monoclonal antibodies 1 mg of polyclonal rabbit anti-rMRP-70 or anti-MRP-160 fragment 1, 2, 3 or 4 antibody of Example 14 or monoclonal anti-rMRP-70 antibody of Example 15 and 0.1 mg Biotin-X-NHS® (Calbiochem) are reacted in 1.0 ml of 0.1M Hepes buffer pH 8.0 for 4 hrs at 4° C. according to the procedure suggested by the manufacturer. The biotinylated antibodies are dialysed at 4° C. against PBS and stored at –80° C.

16.2 Sandwich ELISA

MRP-160, rMRP-70 and MRP-160 fragments are detected by a two-site sandwich ELISA described in Example 12.3.2.

The assay detects rMRP-70 in transformed cells or MRP-160 in cellular lysates of human monocytes, in transformed cells and in body fluids of human patients down to 1.0 ng/ml.

16.3 Test kit for sandwich ELISA

A test kit for the sandwich ELISA of Example 16.2 contains for example:

microtiter plates (Nunc FI)

20 ml of affinity purified polyclonal anti-rMRP-70 rabbit antibodies (1 µg/ml) in 0.05M carbonate buffer pH 9.6

1.0 ml of recombinant rMRP-70 standard solution (1 mg/ml) in TBS containing 0.05% Tween 20

10 ml of biotinylated polyclonal rabbit anti-rMRP-70 antibodies (0.5 µg/ml) in TBS pH 7.4, 0.2% gelatin, 1% BSA, 0.05% Tween 20

10 ml streptavidin-alkaline phosphatase (BRL) 1:5000 in TBS pH 7.4, 0.2% gelatin, 1% BSA, 0.05% Tween 20

200 ml TBS, 0.05% Tween 20

200 ml TBS pH 7.4, 0.2% gelatin, 1% BSA, 0.05% Tween 20

20 ml p-nitrophenyl phosphate (1.0 mg/ml) in diethanolamine buffer (1M, pH 9.8)

calibration curve instruction manual.

Example 17

Detection of Hodgkin Lymphoma by Immunostaining

Lymph node biopsies, skin biopsies or other tissue biopsies are quickly frozen in isopentane cooled by liquid nitrogen and stored at –75° C. 5 µm tissue sections are cut, fixed for 15 min in acetone and dried overnight at room temperature. The sections are rehydrated in PBS for 10 min, then incubated in a 1:100 dilution of anti-rMRP-70 rabbit polyclonal antibody of Example 14.2 for 30 min, rinsed in PBS for 10 min, then incubated in a 1:400 dilution of biotinylated mouse anti-rabbit monoclonal antibody (Dakopatts, Copenhagen, Denmark) for 30 min. The sections are rinsed in PBS for 10 min and treated with the ABComplex™ (avidin complexed with biotinylated peroxidase, Dakopatts) according to the instructions of the manufacturer. The reaction product is developed with the chromogenic substrate AEC/hydrogen peroxide (50 mg aminoethylcarbazole, 33 µl 30 % $H_2O_2$, 5 ml dimethylformamide, 100 ml acetate buffer 0.05M, pH 6.9). The sections are rinsed in acetate buffer for 5 min, counterstained with Mayer's hematoxylin, mounted with glycerin jelly and inspected with a microscope.

The results obtained with biopsy material from different sources are collected in Table 6. Immunostaining using anti-rMRP-70 antisera is clearly restricted to Hodgkin's disease and the related anaplastic large cell lymphomas.

TABLE 6

Immunostaining of Hodgkin lymphoma and other tissue sections

| Tissue source and diagnosis | No. of cases | No. of anti-MRP-70 staining |
|---|---|---|
| lymph node Hodgkin's disease | 36 | 31 |
| lymph node anaplastic large cell lymphomas (Ki-1 positive) | 4 | 4 |
| lymph node other non-Hodgkin lymphomas | 10 | 0 |
| lymph node non-specific lymphadenitis | 4 | 0 |
| skin inflammatory conditions | 4 | 0 |
| adenocarcinoma | 2 | 0 |
| epidermoid carcinoma | 1 | 0 |
| soft tissue sarcoma | 3 | 0 |

Example 18

Pharmaceutical Composition for Parenteral Application

200 μg of rMRP-70 or of MRP-160 are dissolved in 3 ml of 5N human serum albumin. The resulting solution is passed through a bacteriological filter and the filtered solution subdivided under aseptic conditions into 10 vials. The vials are preferably stored in the cold, for example at −20° C.

Likewise pharmaceutical compositions containing 0.5 mg, 1 mg, 2 mg and 5 mg of polyclonal or monoclonal antibodies of Examples 14 and 15 in 3 ml of 5N human serum albumin are prepared. Pharmaceutical compositions of higher concentration are obtained by dissolving 10 mg of monoclonal antibody directed to rMRP-70 (Example 15) in 2 ml of sterilized physiological saline.

We claim:

1. A polypeptide having the amino acid sequence shown in FIG. 1(A–J), or a fragment of said polypeptide which is at least 15 amino acids in length.

2. A polypeptide or fragment according to claim 1 which is of human origin.

3. A fragment according to claim 1 which consists of amino acids 878-1427 of the amino acid sequence given in FIG. 1(A–J), wherein the N-terminus is hydrogen, acyl, the amino acid sequence Asp-Gly-Ile-Asp-Lys-Leu-Asp-Ile-Glu-Phe-Gly or the amino acid sequence Met-Asp-Gly-Ile-Asp-Lys-Leu-Asp-Ile-Glu-Phe-Gly.

4. A polypeptide or fragment according to claim 1 which is a compound wherein amino and/or hydroxyl functions are glycosylated or acylated.

5. A polypeptide or fragment according to claim 1 in the form of a pharmaceutically acceptable salt.

6. A process for the preparation of a polypeptide or a fragment according to claim 1 wherein a solution containing such a polypeptide or fragment is purified by chromatographic methods.

7. A process according to claim 6 wherein the solution containing the polypeptide or fragment is obtained by culturing transformed host cells expressing the desired compound under conditions which allow expression of heterologous polypeptides.

8. A process according to claim 7 wherein said host cells are selected from the group consisting of bacteria, yeast, and a higher organism cell culture.

9. A process according to claim 8 wherein the bacterial host cells are selected from the group consisting of *Escherischia coli, Bacillus subtilis, Bacillus stearothermophilus*, Pseudomonas, Haemophilus and Streptococcus host cells.

10. A process according to claim 8, wherein the yeast host cells are *Saccharomyces cerevisiae* host cells.

11. A process according to claim 8, wherein the higher organism cell culture is a human or non-human animal cell line.

* * * * *

UNITED STATES PATENT AND TRADEMARK OFFICE
CERTIFICATE OF CORRECTION

PATENT NO. : 5,821,336
DATED : OCTOBER 13, 1998
INVENTOR(S) : KAREL GERRIT ODINK ET AL.

It is certified that error appears in the above-identified patent and that said Letters Patent is hereby corrected as shown below:

Title page, section [75], should read:

-- [75] Inventors: Karel Gerrit Odink, Rheinfelden, Switzerland; Lajos Tarcsay, Grenzach-Wyhlen, Germany; Josef Brüggen, Riehen, Switzerland; Walter Wiesendanger, Aesch, Switzerland; Nico Cerletti, Bottmingen, Switzerland; Clemens Sorg, Münster, Germany; Christiane Dewolf-Peeters, Bekkevoort; Jan Delabie, Marke, both Belgium --.

Signed and Sealed this

Thirty-first Day of August, 1999

Attest:

Q. TODD DICKINSON

*Attesting Officer*   *Acting Commissioner of Patents and Trademarks*